United States Patent [19]

Mack

[11] 4,269,731
[45] May 26, 1981

[54] ANTIMONY MERCAPTOCARBOXYLIC ACID ESTER STABILIZERS FOR POLYVINYL CHLORIDE RESIN COMPOSITIONS AND PROCESS

[75] Inventor: Gerry Mack, Jackson Heights, N.Y.

[73] Assignee: Argus Chemical Corporation, Brooklyn, N.Y.

[21] Appl. No.: 69,959

[22] Filed: Aug. 27, 1979

[51] Int. Cl.³ .................. C09K 15/12; C08K 5/09; C08K 5/36
[52] U.S. Cl. .................. 252/400 R; 260/45.75 R; 260/45.75 K; 260/45.75 J; 260/45.75 B; 260/429.7; 260/429.9; 260/446; 260/455 R; 260/45.7 S
[58] Field of Search .............. 252/400 R; 260/45.7 S, 260/45.75 R, 45.75 K, 45.75 J, 45.75 B, 429.7, 429.9, 446, 455 R

[56] References Cited

U.S. PATENT DOCUMENTS

| | | | |
|---|---|---|---|
| 2,680,726 | 6/1954 | Weinberg et al. | 260/446 |
| 2,684,956 | 7/1954 | Weinberg et al. | 260/446 |
| 3,305,580 | 2/1967 | Homberg et al. | 260/45.85 R |
| 3,340,285 | 9/1967 | Romes et al. | 260/446 |
| 3,466,261 | 9/1969 | Mauz | 260/45.75 R |
| 3,530,158 | 9/1970 | Leebrick et al. | 260/446 |
| 3,565,930 | 2/1971 | Kauder et al. | 260/429.7 |
| 3,565,931 | 2/1971 | Brecker | 260/429.7 |
| 3,632,538 | 1/1972 | Kauder | 252/406 |
| 3,887,508 | 6/1975 | Dieckmann | 252/406 |
| 4,029,618 | 6/1977 | Dieckmann | 260/23 XA |

*Primary Examiner*—Richard E. Schafer
*Assistant Examiner*—Irwin Gluck

[57] ABSTRACT

Antimony mercaptocarboxylic acid esters are provided having the formula:

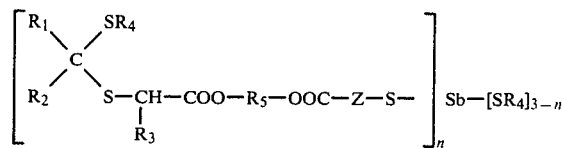

wherein:
$R_1$ is selected from the group consisting of hydrogen, alkyl having from one to about eighteen carbon atoms and alkylene linked with $R_2$ in a ring having from three to about eight carbon atoms;

$R_2$ is selected from the group consisting of alkyl having from one to about eighteen carbon atoms, phenyl, and alkylene linked with $R_1$ in a ring having from three to about eight carbon atoms;

$R_3$ is selected from the group consisting of hydrogen and alkyl having from one to three carbon atoms;

$R_4$ is selected from the group consisting of alkyl, aryl, alkylaryl, alkoxycarbonyl-alkylene and acyloxyalkylene having from three to about twenty carbon atoms, the alkylene having from two to about six carbon atoms;

$R_5$ is selected from the group consisting of alkylene and cycloalkylene having from one to about eighteen carbon atoms, and such groups having from one to four hydroxyl groups;

Z is a bivalent alkylene group having from one to five carbon atoms and carrying the sulfur in a position alpha or beta to -OOC-; and n is a number from 1 to 3.

A process for preparing such antimony compounds is also provided, as well as predecessor intermediates, and stabilizer compositions for polyvinyl chloride resin compositions comprising such antimony compounds, if desired with other polyvinyl chloride resin stabilizers.

56 Claims, No Drawings

ANTIMONY MERCAPTOCARBOXYLIC ACID ESTER STABILIZERS FOR POLYVINYL CHLORIDE RESIN COMPOSITIONS AND PROCESS

Polyvinyl chloride resin compositions used for the manufacture of rigid articles such as pipe and profiles are processed nowadays by extrusion in multi-screw extruders. Multi-screw extruders differ from the older single-screw extruders, calenders and blow-molding machines in retaining the polyvinyl chloride resin composition being processed for a much shorter period of time. Such polyvinyl chloride resin compositions are usually pigmented, and they are also highly lubricated, by virtue of the addition of substantial amounts of lubricants such as waxes, mineral oil, and calcium stearate, so that under the positive displacement pumping action of the multi-screw extruder they can be processed at any desired rate.

Thus, the polyvinyl chloride resin compositions may not be subjected to the rather elevated temperatures, of the order of 375° F. and higher, required to bring the composition to an extrudable, softened condition, for much longer than thirty minutes, and frequently only for as little as five to ten minutes.

Conventional heat stabilizer compositions are not suited for use with such rigid polyvinyl chloride resin compositions. The highly lubricated compositions that are especially formulated for extrusion in such machines do not require stabilization against long heating times at 375° F. What is required, especially for light-colored compositions, is resistance to the development of any significant discoloration during the first five to ten or twenty minutes of heating, so as to avoid change in the color. Such discoloration is referred to as "early yellowing".

This discoloration conventional heat stabilizers are not generally formulated to prevent. While long term heat stability has been a prerequisite, an early discoloration could be tolerated if it did not deepen significantly with continued heating, since the art tolerated discoloration to the extent necessary to avoid degradation in physical properties during long term heating.

The highly lubricated formulations that have been developed for extrusion in these machines contain substantial quantities of lubricants, such as calcium stearate, frequently more lubricant than stabilizer. Typically from 0.6 to 1 part per hundred, and sometimes as much as two parts per hundred of lubricant, are used with from 0.3 to 0.5 part per hundred of an organotin stabilizer containing 12% tin or less. Such proportions are to be contrasted with the proportions used in conventional extrudable compositions for use with single-screw extruders, where from 1 to 1.5 parts per hundred of stabilizers containing 18% tin or 21 to 26% tin is used with a maximum of about 0.5 part per hundred of the lubricant. Since the most popular lubricant has been calcium stearate, the change in relative proportions has meant a considerable change in the tin/calcium ratio.

Moreover, since calcium stearate has a tendency to impart a yellow discoloration of its own, the prevention of early yellowing in such highly lubricated extrudable formulations has become correspondingly more difficult.

Among the organotin stabilizers proposed in recent years are the organotin thioacetals and thioketals. Several structural variations have been suggested.

U.S. Pat. No. 3,078,290, patented Feb. 19, 1963 to Hechenbleikner, Bresser and Homberg, provides dihydrocarbon tin salts of acids having a thioacetal or thioketal grouping and belonging to one of the following groups:

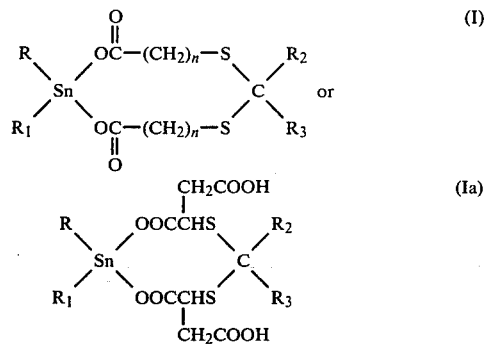

where n is an integer from 1 to 8, R and $R_1$ are alkyl, aralkyl or aryl and $R_2$ and $R_3$ are hydrogen, alkyl, alkenyl, aralkyl, aryl, hydroxyaryl, alkoxyaryl or taken together complete a cyclohexane ring, i.e., the pentamethylene radical.

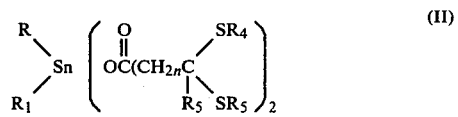

where n, R and $R_1$ are as defined above, $R_4$ and $R_5$ are alkyl, aralkyl, aryl, mercaptocarboxylic acid or mercaptocarboxylic acid ester and $R_6$ is hydrogen, alkyl benzyl or aryl.

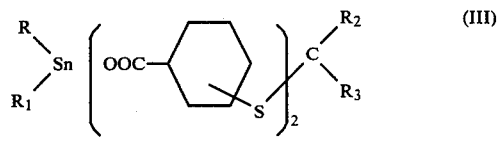

where R, $R_1$, $R_2$ and $R_3$ are defined above.

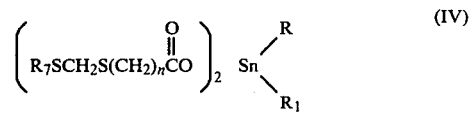

where n, R and $R_1$ are as defined above and $R_7$ is alkyl, aralkyl or aryl.

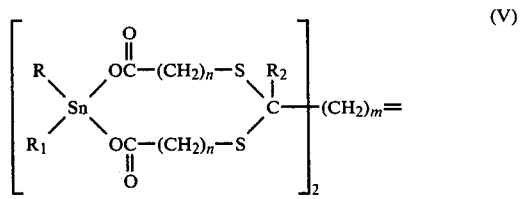

where R, $R_1$, and n are defined as above, $R_8$ is alkyl, aralkyl or aryl and m is an integer from 0 to 8.

In another form certain thioacetals and thioketals are mixed with dihydrocarbon tin oxides or sulfides.

U.S. Pat. No. 3,196,129, patented July 20, 1965 to Hechenbleikner, Bresser and Homberg, provides not only such dihydrocarbon tin salts of acids having a thioacetal or thioketal grouping, but also monohydrocarbon and trihydrocarbon tin salts of acids having a thioacetal or thioketal grouping. Such compounds belong to one of the following groups:

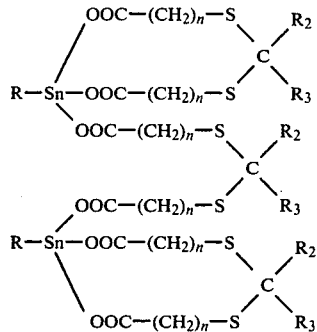 (A)

where n, R, $R_2$ and $R_3$ are as defined above, in U.S. Pat. No. 3,078,290.

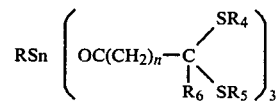 (B)

where n, R, $R_4$, $R_5$ and $R_6$ are as defined above, except that $R_4$ and $R_5$ are carboxylic, not thiocarboxylic acid or acid ester.

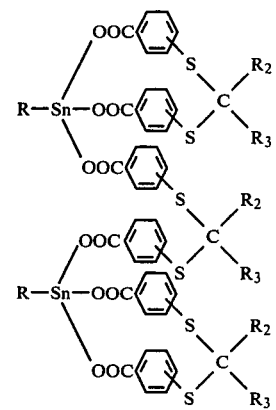 (C)

where R, $R_2$ and $R_3$ are as defined above.

$$RSn(OOC(CH_2)_nSCH_2SR_7)_3 \quad (D)$$

wherein n, R, and $R_7$ are as defined above.

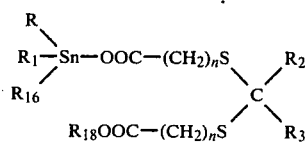 (E)

where n, R, $R_1$, $R_2$ and $R_3$ are as defined above; $R_{16}$ is alkyl, aralkyl or aryl and $R_{18}$ is H or

Preferably, $R_{18}$ is

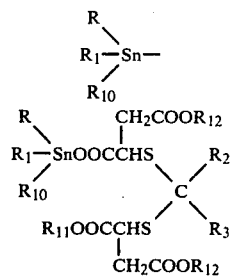 (F)

where R, $R_1$, $R_2$, $R_3$ and $R_{10}$ are as defined above and $R_{11}$, $R_{12}$ and $R_{13}$ are selected from the group consisting of hydrogen and

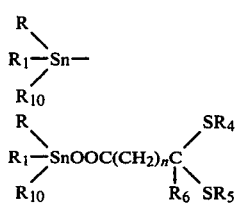 (G)

where n, R, $R_1$, $R_4$, $R_5$, $R_6$ and $R_{10}$ are as defined above.

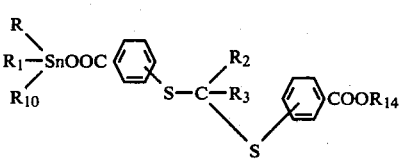 (H)

where R, $R_1$, $R_2$, $R_3$ and $R_{10}$ are as defined above, and $R_{14}$ is selected from the group consisting of hydrogen and

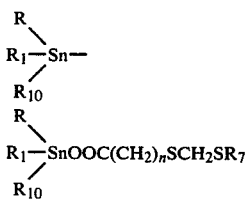 (J)

where n, R, $R_1$, $R_7$ and $R_{10}$ are as defined above.

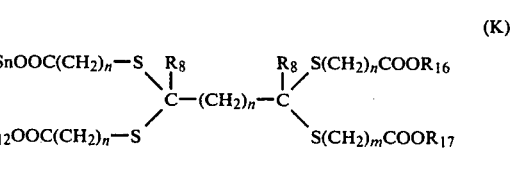 (K)

where m, n, R, $R_1$, $R_8$ and $R_{10}$ are as defined above, and $R_{15}$, $R_{16}$ and $R_{17}$ are selected from the group consisting of hydrogen and

While the formulae are written for the monomeric materials, many of them also exist in a polymeric form closely approximating the monomeric formulae.

In another form of the invention, certain thioacetals and thioketals are mixed with dihydrocarbon tin oxides or sulfides or with monohydrocarbon stannoic acids or monohydrocarbon tin alcoholates or trihydrocarbon tin oxides.

U.S. Pat. No. 3,544,510, patented Dec. 1, 1970 to Stapfer, provides monomeric or polymeric mercaptals of the unit structure

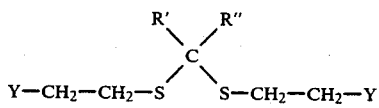

wherein Y is a —COOR or —OOCR group, and R, R', and R" are monovalent hydrocarbon groups, which mercaptals contain chemically bound or in intimate physical mixture an alkyl stannoic or alkyl thiostannoic acid.

These correspond to the formula

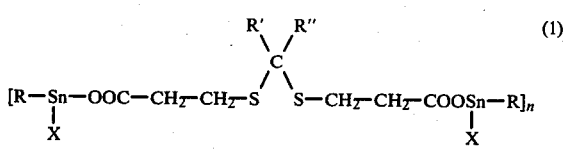

wherein X is oxygen or sulfur, and n=1 to ∞, or are mixtures of compounds

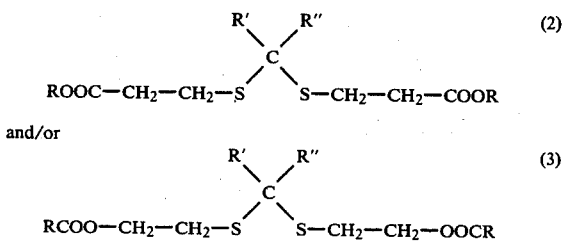

with 1 to 10, preferably about 5% by weight or about 0.1 mole percent, calculated on the mercaptal, of a stannoic or thiostannoic acid RSnOOH or RSnSSH. The stannoic and thiostannoic acid may also be used in form of their polymers [RSnX$_{1.5}$]$_m$ wherein X is oxygen or sulfur, and m is a number between 2 and ∞.

U.S. Pat. No. 4,111,873, patented Sept. 5, 1978 to Cordes, proposes very similar compounds without the tin, of the formula:

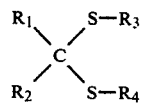

wherein R$_1$ and R$_2$ are independently selected from hydrogen, alkyl, aryl, alkyl- or alkoxy-substituted aryl, aralkyl, alkyl- or alkoxy-substituted aralkyl, or taken together form an alkylene radical of three to nine carbon atoms; R$_3$ and R$_4$ are independently selected from alkyl of at least 4 carbon atoms, carbalkoxyalkyl, aryl, alkyl- or alkoxy-substituted aryl, aralkyl, alkyl-or alkoxy-substituted aralkyl or taken together form thiodimethylene, an ortho-arylene radical, an alkyl-or alkoxy-substituted ortho-arylene radical, or an alkylene radical of two to four carbon atoms; in combination with a divalent metal salt of a carboxylic acid of seven to twenty carbon atoms, or mixture of such metal salts.

The organotin mercaptocarboxylic acid esters are widely recognized as the most effective organotin stabilizers, having a tin content of about 18% Sn. The position of the organotin mercaptocarboxylic acid esters has been challenged in recent years by the provision of stabilizers containing a higher proportion of tin, from about 21 to about 26% Sn, referred to as "high efficiency" organotins. The latter are exemplified by the organotin mercaptocarboxylic acid ester sulfides of U.S. Pat. Nos. 3,565,930, 3,565,931, 3,632,538 and 3,817,915. However, a high tin content is not a determinative factor in preventing the development of early discoloration, as exemplified by the organotin sulfides, which offer the highest tin and sulfur contents per organotin group, and yet are not the most effective in this respect, affording a poor initial color, particularly.

While there are organotin stabilizers which are capable of lessening or inhibiting early discoloration, in recent years the organotins have become extremely expensive, and in short supply, with the result that the low cost products such as pipe and profiles have not been able to bear the cost of such stabilizers, and the art has had to turn to substitute systems which are less expensive.

One such type of system blends the organotin compound with an additional stabilizer.

U.S. Pat. No. 3,209,012, patented Sept. 28, 1965, to Miller, Hechenbleikner and Homberg, provides substituted oxathiolanes having the formula:

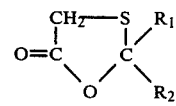

where R$_1$ and R$_2$ individually are hydrogen, alkenyl, alkyl, aralkyl or aryl or together are an alkylene radical having a chain of four to five carbon atoms.

These are useful as stabilizers for halogen-containing materials with tin compounds such as dialkyltin oxides and dialkyltin acylates.

U.S. Pat. No. 3,305,580, patented Feb. 21, 1967, to Homberg, Hechenbleikner and Miller provides unsaturated sulfur-containing carboxylic acids and the salts and esters of such acids having the formula R$_1$S(CH$_2$)$_n$—COOR$_2$ where R$_1$ is alkenyl, aralkenyl or cycloalkenyl in which the aliphatic or cycloaliphatic double bond is attached to the carbon atom directly attached to the sulfur atom and R$_2$ is hydrogen, alkyl, ammonium or a metal, e.g. sodium or potassium, and n is an integer up to 10, preferably 1 or 2.

These compounds are useful as stabilizers for halogen-containing resins, particularly when used with tin compounds such as dialkyltin oxide and dialkyltin acrylates.

U.S. Pat. No. 3,654,222, patented Apr. 4, 1972, to Stapfer and Shah, provides combinations of an alkyltin carboxylate and a monoalkyltin sulfide, in the form of:

(A) a binary system comprising a dihydrocarbyltin carboxylate of the general formula:

$$[R_2Sn(OCOR')_2]_m$$

and a monohydrocarbyltin sulfide of the general formula:

$$RSnS_{1.5}$$

or any sulfhydrated derivative thereof, such as

RSnSH generally referred to as hydrocarbyl thiostannoic acids. The term monohydrocarbyl tin sulfide as used therein includes the compounds generally known as monohydrocarbyl thiostannoic acids, or, (B) a tertiary system comprising the above binary stabilizer system and, acting as an anti-oxidant, an alkyl substituted monomeric (I) phenol of the general formulae:

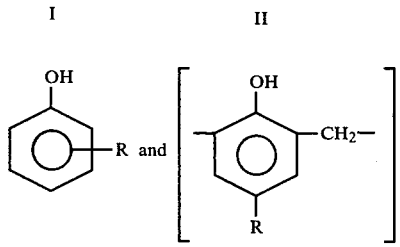

In all of the above formulae, R denotes alkyl radicals having one to twelve carbons, R' is the organic moiety of a mono-or dibasic carboxylic acid, and m is an integer of at least 1 and n is an integer of at least 2.

Stabilizer systems based on antimony compounds are less expensive, but however formulated, have not been capable of inhibiting the development of a yellow discoloration during the first five or ten minutes of heating. The yellow discoloration has been sufficiently intense, after only ten minutes of heating, that such stabilizer systems despite their lower cost have not been competitive with organotin systems. Antimony-based stabilizers have also been characterized by poor storage life, with the formation of red, orange or black precipitates (presumably antimony sulfides and metallic antimony, respectively) being known to occur. Moreover, polyvinyl chloride compositions stabilized with antimony-based stabilizers have had a greater tendency to discolor on exposure to sunlight than similar compositions with stabilizers not based on antimony.

A number of patents have suggested the use of antimony compounds, particularly sulfur-containing compounds such as the antimony mercaptides. These include U.S. Pat. Nos. 2,680,726, 2,684,956, 3,340,285, 3,999,220, 3,466,261 and 3,530,158. These patents disclose various types of organic sulfur-containing antimony compounds, but none have been adequate in inhibiting the development of an early yellow discoloration, in the processing of rigid polyvinyl chloride resin compositions.

Weinberg, Johnson and Banks U.S. Pat. No. 2,680,726 patented June 8, 1954 suggested the use of antimony mercaptocarboxylic acid esters of the formula $Sb(SRCO_2R')_3$, where R is alkylene, arylene or aralkylene and R' is a substituted or unsubstituted alkyl or mixed alkyl-aryl group. Among the compounds named are $Sb(SCH_2CO_2C_9H_{19})_3$ a mobile slightly yellow liquid; Sb—S,S',S''-tris(octadecyl thiomalate); $Sb(SCH_2CO_2C_{10}H_{21})$; Sb—S',S''-tris(glyceryl monoricinoleate-monomercaptoacetate) and Sb—S,S',S''-tris(dihydroabietyl mercaptoacetate).

German patent No. 1,114,808 to Deutsche Advance proposed antimony compounds of the formula:

$$(XS)_2SbS(CH_2)_xCOO\text{—}A\text{—}COO(CH_2)_xSSb(SX)_2,$$

where x is an integer from 1 to 4, A an alkylene residue of up to ten carbon atoms, with or without OH groups, or merely a bond, and SX is the residue (having from eight to eighteen carbon atoms) of an aliphatic or aromatic mercaptan, or of an ester of a thioalcohol or thio acid, as stabilizers for polyvinyl halide resins.

Chemische Werke Barlocher British Pat. No. 1,194,414, published June 10, 1970, suggested antimony compounds of the formula:

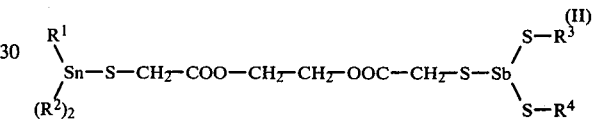

wherein:
R¹ is an organic group (which may contain tin and/or antimony atoms) which is linked to the tin atom via a carboxylic group or a thio group and is the radical of an aliphatic carboxylic acid having at least four carbon atoms or of a mercaptan;
R² is an alkyl radical;
R³ and R⁴ are organic groups linked to the sulfur atom via a carbon atom and are together with the sulfur atom radicals of mercapto compounds; and

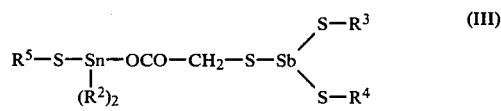

wherein:
R⁵ is an organic group (which may contain tin and/or antimony atoms) which is linked to the sulfur atom via a carbon atom;
R², R³ and R⁴ have the designations assigned to them in Formula II.

These are mixed compounds containing both antimony and tin in the molecule.

East German Pat. No. 71,360 patented Feb. 20, 1970 suggested antimony mercaptocarboxylate esters such as Sb-tris (2-ethylhexyl thioglycolate), used together with the corresponding organotin mercapto carboxylic ester.

Dieckmann, U.S. Pat. No. 3,887,508, patented June 3, 1975, has suggested that the stabilizing effectiveness of such antimony compounds can be improved by combining them with a metal carboxylate. Dieckmann proposed that antimony sulfur-containing compounds of the general formula $Sb(SR)_3$ (where R is a hydrocarbon or substituted hydrocarbon radical; SR the residue of a mercaptan or mercaptoalcohol or a mercaptocarboxylic acid ester) be improved by combining therewith an alkali metal or alkaline earth metal salt of monocarboxylic and dicarboxylic acids of the type $(RCXX)_nM$ wherein the group RCXX is the carboxylate and/or thiocarboxylate group of an aliphatic or aromatic mono- or polyfunctional acid containing, for example, about $C_2$–$C_{54}$ carbon atoms; R is a hydrocarbon or substituted hydrocarbon radical; X is oxygen and/or sulfur; n is an integral number from 1 to 2 and M is an alkali or alkaline earth metal, for example, sodium, potassium, lithium, magnesium, calcium, strontium and barium. This class of course includes calcium stearate. According to Dieckmann, such combinations exhibit a synergism in long term heat stability, in comparison with a standard resin formulation containing neither antimony organic compound nor metal carboxylate. The results in the working Examples, for instance, Table II, column 7, are reported in terms of the length of time required for the resin composition to develop the same degree of discoloration as a control composition without either stabilizer after ten minutes of heatng. There is no consideration given nor any report of the effectiveness of the stabilizer combinations in preventing the development of early discoloration, including the yellow discoloration imparted by the metal carboxylate.

In fact, these compositions are not capable of preventing the development of early discoloration. The metal carboxylate continues to contribute to early discoloration, just as it does in the absence of the antimony compound. Not only does it not enhance the effectiveness of the antimony compound in this respect; it worsens it. Compositions containing the antimony compound and the metal carboxylate develop a more intense yellow discoloration after the first five or ten minutes of heating than the antimony compound taken alone, although the long term stability may be extended.

Phenolic antioxidants, especially hindered phenols, have long been known as stabilizers for polyvinyl chloride resin compositions, particularly when used in combinations with other stabilizers. One of the first disclosures of the use of hindered phenols for this purpose is in U.S. Pat. No. 2,564,646, patented August 14, 1951 to William E. Leistner, Arthur C. Hecker and Olga H. Knoepke. The effectiveness of phenols is discussed in the *Encyclopedia of Polymer Science and Technology* Volume 12 (1970), page 752. A problem with phenols is their tendency to impart a yellow discoloration to the compound on their own, which puts them in the category of calcium stearate; the result is an initial yellow discoloration which remains during the initial stages of heating, and then worsens. This of course disqualifies them; they are incapable of preventing the development of an early discoloraton.

Dieckmann U.S. Pat. No. 4,029,618, patented June 14, 1977 claims that the early color heat performance of antimony organic sulfur containing compounds is significantly improved if they are combined with ortho-dihydric phenols. Improvements in long term heat stability also are achievable, according to the patent, and in addition, the compositions are inserted to be liquids which are shelf-stable at ambient temperatures. Dieckmann points out that liquid antimony stabilizer compositions tend to deteriorate on standing, as observed by the formation and/or precipitation of solids in the liquid compounds, forming heterogeneous liquids, which increase the problems of measuring and mixing the antimony compounds into vinyl halide resins for stabilization. This problem, it is asserted, is overcome by incorporating the ortho-dihydric phenol with the liquid antimony stabilizer. In these combinations, metal carboxylates, and particularly calcium stearate, can also be incorporated to achieve the advantages of the previously issued Dieckmann U.S. Pat. No. 3,887,508.

In accordance with the present invention, a new class of antimony mercaptocarboxylic acid esters is provided, having the formula:

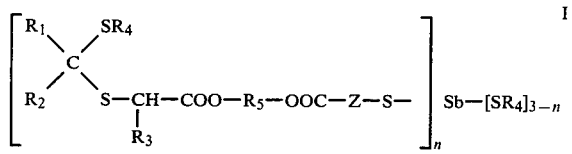

wherein:
R₁ is selected from the group consisting of hydrogen, alkyl having from one to about eighteen carbon atoms and alkylene linked with R₂ in a ring having from three to about eight carbon atoms;

R₂ is selected from the group consisting of alkyl having from one to about eighteen carbon atoms, phenyl, and alkylene linked with R₁ in a ring having from three to about eight carbon atoms;

R₃ is selected from the group consisting of hydrogen and alkyl having from one to three carbon atoms;

R₄ is selected from the group consisting of alkyl, aryl, alkylaryl, alkoxycarbonyl-alkylene and acyloxyalkylene having from three to about twenty carbon atoms, the alkylene having from two to about six carbon atoms;

R₅ is selected from the group consisting of alkylene and cycloalkylene having from one to about eighteen carbon atoms, and such groups having from one to four hydroxyl groups;

Z is a bivalent alkylene group having from one to five carbon atoms and carrying the sulfur in a position alpha or beta to —OOC—; and n is a number from 1 to 3.

These compounds are characterized by an unusually high sulfur content, and resulting stabilizing effectiveness for rigid polyvinyl chloride resin compositions.

These compounds are obtained in a novel synthesis of five steps:

(1) reaction of an aldehyde or ketone with an α-mercaptocarboxylic acid, resulting in addition of the mercapto group of the α-mercaptocarboxylic acid to the keto group of the aldehyde or ketone;

(2) reaction of the resulting substituted cyclic thiolactone with a mercaptide, which can be a mercaptocarboxylic acid ester, mercaptoalcohol ester or mercaptan, and an acid catalyst having a minimum ionization constant $K_{ion}$ in water at least $1\times 10^{-4}$, i.e., a pK value of at most 4, resulting in opening of the lactone ring, and the formation of the corresponding mercaptocarboxylic acid, with the organic radical of the mercaptide becoming attached to the keto carbon atom of the starting aldehyde or ketone;

(3) esterification of the mercaptocarboxylic acid with a glycol or higher polyol to give the polyol monoester;

(4) esterification of the free alcohol group of the polyol monoester with a mercaptocarboxylic acid to form the corresponding ester with a free mercapto group; and (5) reaction of the free mercapto group of this ester with a polyvalent metal compound, such as antimony trioxide, to form the corresponding polyvalent metal mercaptocarboxylic acid ester salt.

Reaction (1) is known:

(a) *Bulletin of the Chemical Society of Japan* 45 913-15 (1972)
(b) *J. Heterocyclic Chemistry* 14 1035 (1977)
(c) *Acta Chem. Scand.* A30 (1976) No. 6
(d) U.S.Pat. No. 3,209,012.

Reaction (2) is believed to be new, and so is the synthesis including it in combination with reactions (1) and (3) to (5).

The reaction products from steps (2), (3) and (4) of this synthesis are predecessor intermediates not only to the antimony mercaptocarboxylic acid ester of the invention but also to other monovalent and polyvalent metal mercaptocarboxylic acid ester salts, such as the Sn, Ca, Zn, Cd, Mg, Ba, Pb, and Li compounds, and are further considered to be new compounds. The invention accordingly provides the following additional new compounds:

Mercaptocarboxylic acids having the formula:

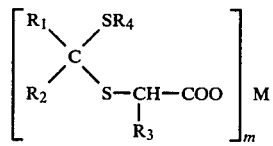

wherein:

$R_1$ is selected from the group consisting of hydrogen, alkyl having from one to about eighteen carbon atoms and alkylene linked with $R_2$ is a ring having from three to about eight carbon atoms;

$R_2$ is selected from the group consisting of alkyl having from one to about eighteen carbon atoms, phenyl, and alkylene linked with $R_1$ in a ring having from three to about eight carbon atoms;

$R_3$ is selected from the group consisting of hydrogen and alkyl having from one to three carbon atoms;

$R_4$ is selected from the group consisting of alkyl, aryl, alkylaryl, alkoxycarbonyl-alkylene and acyloxyalkylene having from three to about twenty carbon atoms, the alkylene having from two to about six carbon atoms;

M is a monovalent or polyvalent metal cation such as Sn, Ca Zn, Cd, Mg, Ba, Pb, and Li; and m is a number from 1 not exceeding the valence of M, any remaining bonds of the valence not taken up by the mercaptocarboxylic acid group being taken up by hydrogen H.

Polyol mercaptocarboxylic acid monoesters having the formula:

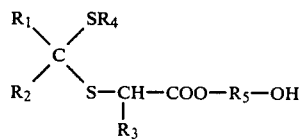

wherein $R_1$ is selected from the group consisting of hydrogen, alkyl having from one to about eighteen carbon atoms and alkylene linked with $R_2$ in a ring having from three to about eight carbon atoms;

$R_2$ is selected from the group consisting of alkyl having from one to about eighteen carbon atoms, phenyl, and alkylene linked with $R_1$ in a ring having from three to about eight carbon atoms;

$R_3$ is selected from the group consisting of hydrogen and alkyl having from one to three carbon atoms;

$R_4$ is selected from the group consisting of alkyl, aryl, alkylaryl, alkoxycarbonyl-alkylene and acyloxyalkylene having from three to about twenty carbon atoms, the alkylene having from two to about six carbon atoms; and $R_5$ is selected from the group consisting of alkylene and cycloalkylene having from one to about eighteen carbon atoms; and such groups having from one to four hydroxyl groups.

Esters of IV with a mercaptocarboxylic acid of the type HS—Z—COOH:

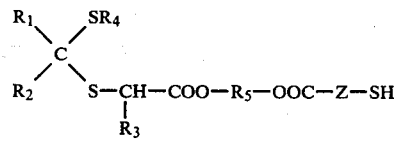

wherein:

$R_1$, $R_2$, $R_3$, $R_4$, $R_5$ are as above, and Z is a bivalent alkylene group having from one to five carbon atoms and carrying the sulfur in a position alpha or beta to —OOC—.

Compounds IV are valuable intermediates not only for the preparation of antimony compounds, but also for other monovalent and polyvalent metal compounds such as the tin compounds which are also polyvinyl chloride resin stabilizers.

Further in accordance with the invention, stabilizer compositions for polyvinyl chloride resin compositions are provided comprising such antimony compounds, if desired with other polyvinyl chloride resin stabilizers, as well as polyvinyl chloride resin compositions comprising a stabilizing amount of such antimony mercaptocarbocylic acid esters and/or stabilizer compositions containing these esters.

In the first reaction of the synthesis of the invention, equimolar quantities of ketone or aldehyde $R_1R_2C=O$ and of an α-mercaptocarboxylic acid are reacted under azeotroping water-removing conditions, optionally with an acid catalyst, in a refluxing inert solvent such as toluene:

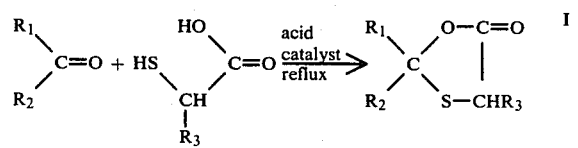

$R_1$, $R_2$, $R_3$ = hydrocarbon group of one to thirty carbons and $R_1$ and $R_3$ can also be hydrogen.

Next, there is added one mole of a mercaptide and an acid catalyst, if an acid catalyst is not used in the first reaction, and which can be an α- or β-mercaptocarboxylic acid ester, mercaptoalcohol ester, or aryl mercaptan R₄SH, and reaction is continued under reflux for several hours to form the corresponding acid.

The acid catalyst has an ionization constant $K_{ion}$ in water of at least $1 \times 10^{-4}$, i.e., a pK value of at most 4.

Exemplary acid catalysts are hydrobromic acid, hydrochloric acid, formic acid, methanesulfonic acid, phosphoric acid, phosphorus acid, perchloric acid, sulfuric acid, thiodiacetic acid, chloroacetic acid, cyclohexylidenebis (thioacetic acid), cyclohexen-1-yl thioacetic acid, citric acid.

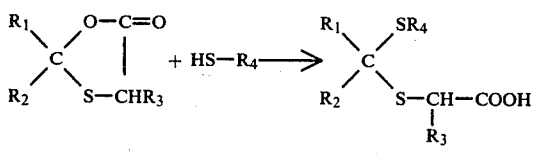

$R_4$ = residue of the mercaptide.

The reaction also requires heating at a temperature within the range from about 100° to about 180° C., preferably from about 100 to about 140° C., for from about two to about ten hours. An inert solvent is desirable, but not essential.

Stoichiometric molar proportions are necessary. An excess of mercaptide is desirable, to aid in driving the reaction to completion.

It is unnecessary to recover unreacted ingredients, since these do not interfere with the third stage of the synthesis, and the reaction mixture can be used as is in the third stage, adding polyol and catalyst directly thereto.

In the third stage, the acid is esterified with one mole of polyol HOR₅OH, again with an acid catalyst, and refluxing toluene to remove the water of reaction as the azeotrope, to give the polyol monoester:

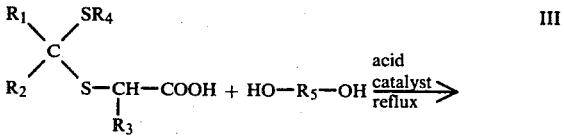

-continued

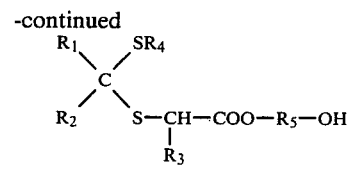

$R_5$ = divalent aliphatic or cycloaliphatic residue from polyol.

The synthesis of the mercaptocarboxylic acid ester is completed by the esterification of IV with the same or another mercaptocarboxylic acid:

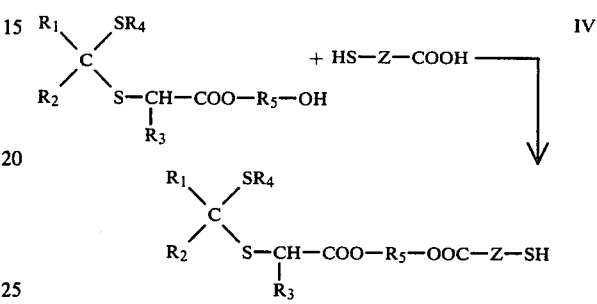

From this mercaptocarboxylic acid ester the antimony mercaptocarboxylic acid ester is conveniently prepared by heating the mercaptoester with antimony trioxide, and eliminating the reaction water by azeotroping with an immiscible solvent, or by applying vacuum to the warm solution. This is done with three moles of the mercaptocarboxylic acid ester, or with two moles of the mercaptocarboxylic acid ester and one mole of another mercaptocarboxylic acid ester, or with one mole of the mercaptocarboxylic acid ester and two moles of another mercaptocarboxylic acid ester. The three reactions forming these three kinds of antimony compounds are as follows:

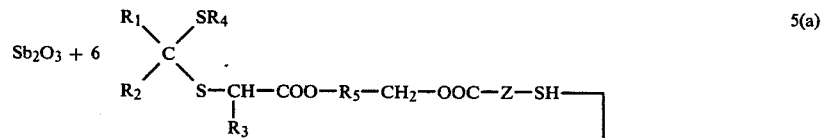

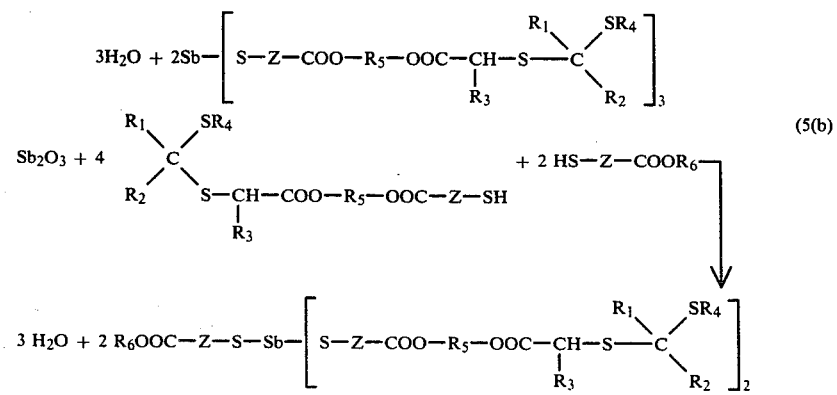

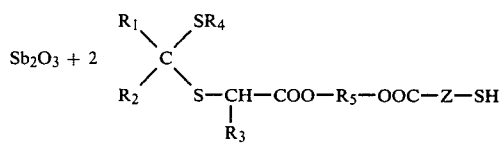

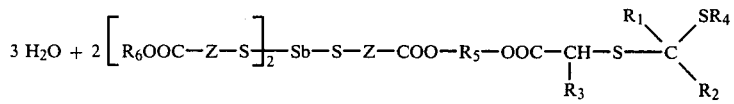

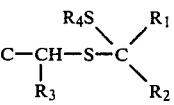

$R_6$ = alkyl, cycloalkyl or aryl of one to eighteen carbon atoms

In the event that a mercaptocarboxylic acid be included in the reaction (5) mixture, the resulting antimony mercaptocarboxylic acid ester can be a polymer having the general formula:

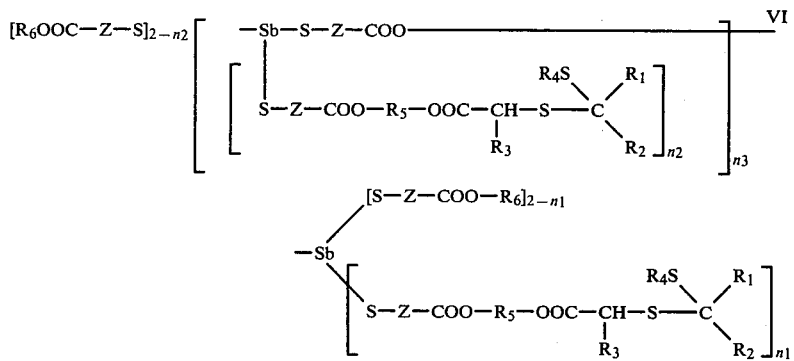

wherein:
- $R_1$ is selected from the group consisting of hydrogen, alkyl having from one to about eighteen carbon atoms and alkylene linked with $R_2$ in a ring having from three to about eight carbon atoms;
- $R_2$ is selected from the group consisting of alkyl having from one to about eighteen carbon atoms, phenyl, and alkylene linked with $R_1$ in a ring having from three to about eight carbon atoms;
- $R_3$ is selected from the group consisting of hydrogen and alkyl having from one to about twenty carbon atoms;
- $R_4$ is selected from the group consisting of alkyl, aryl, alkylaryl, alkoxycarbonyl-alkylene and acyloxyalkylene having from three to about twenty carbon atoms, the alkylene having from two to about six carbon atoms;
- $R_5$ is selected from the group consisting of alkylene and cycloalkylene having from one to about eighteen carbon atoms; and such groups having from one to four hydroxyl groups;
- $R_6$ is selected from the group consisting of alkyl, cycloalkyl, and aryl having from one to about eighteen carbon atoms;
- Z is a bivalent alkylene group having from one to five carbon atoms and carrying the sulfur in a position alpha or beta to —OOC—;
- $n_1$ and $n_2$ are the number of groups, and are integers from 0 to 2; but at least one of $n_1$ and $n_2$ is 1 or 2; and
$n_3$ is the number of $$\left[\begin{array}{c} -Sb-S-Z-COO-\phantom{XXXXXXXXXX} \\ | \\ S-Z-COO-R_5-OOC-CH-S\underset{R_3}{\overset{R_4S\phantom{XX}R_1}{\diagdown\phantom{X}\diagup}}C\underset{R_2}{\phantom{X}} \end{array}\right]$$

groups, and is a number from 0 to 10, and preferably from 0 to 1.

The —S—Z—COO— groups are derived from mono- or poly-α- and β-mercaptocarboxylic acids and esters by removal of the hydrogen atom of the mercapto and/or COOH groups. These groups can be the same or different in the compound.

The groups include the aliphatic acids and esters which contain at least one mercapto group, such as, for example, mercaptoacetic acid, α- and β-mercaptopropionic acid, α- and β-mercaptobutyric acid, α- and β-mercaptovaleric acid, α- and β-mercaptohexanoic acid, thiomalic acid, α- and β-mercaptoadipic acid, and α- and β-mercaptopimelic acid, and the $R_6$ esters of each of these.

$R_5$ is derived from a dihydric alcohol, such as glycols containing from two to about fifteen carbon atoms, including ethylene glycol; propylene glycol; diethylene glycol; di-propylene glycol; tetramethylene glycol; neopentyl glycol and decamethylene glycol; 2,2,4-trimethylpentane-diol; 2,2,4,4-tetramethyl cyclobutanediol; cyclohexane-1,4-dimethanol; and polyols such as glycerol, trimethylolethane, mannitol, sorbitol, erythritol, dipentaerythritol, pentaerythritol, and trimethylol propane.

In reaction (1), the mercaptocarboxylic acid must have the mercapto group in the α-position to the carboxylic acid group. β-Mercaptocarboxylic acids do not yield the desired reaction product II.

On the other hand, in reaction (3) any polyol can be used, and in reaction (4) any mercaptocarboxylic acid, including not only mercaptocarboxylic acids but also mercaptocarboxylic acid esters, and mercaptoalcohol carboxylic acids and esters having a free mercapto group.

No reference to reaction (2) has been found in the literature. However, there is significant evidence that the reaction proceeds in this way, inasmuch as the titratable acidity of the reaction mixture increases in the course of the reaction, indicating that the reactants which are nonacidic react to form a titratable acid. At the same time, the disappearance of the titratable mercapto function —SH of the mercaptocarboxylic acid ester starting material is also confirmed by analysis. Infra-red and proton magnetic resonance spectra are consistent with the structure indicated of the reaction product.

The remaining reactions (3), (4) and (5) of the synthesis are known reactions, and proceed under known conditions with the expected but novel reaction product being formed in each case.

The following antimony mercaptocarboxylic acid esters are representative of the antimony mercaptocarboxylic acid esters falling within the present invention.

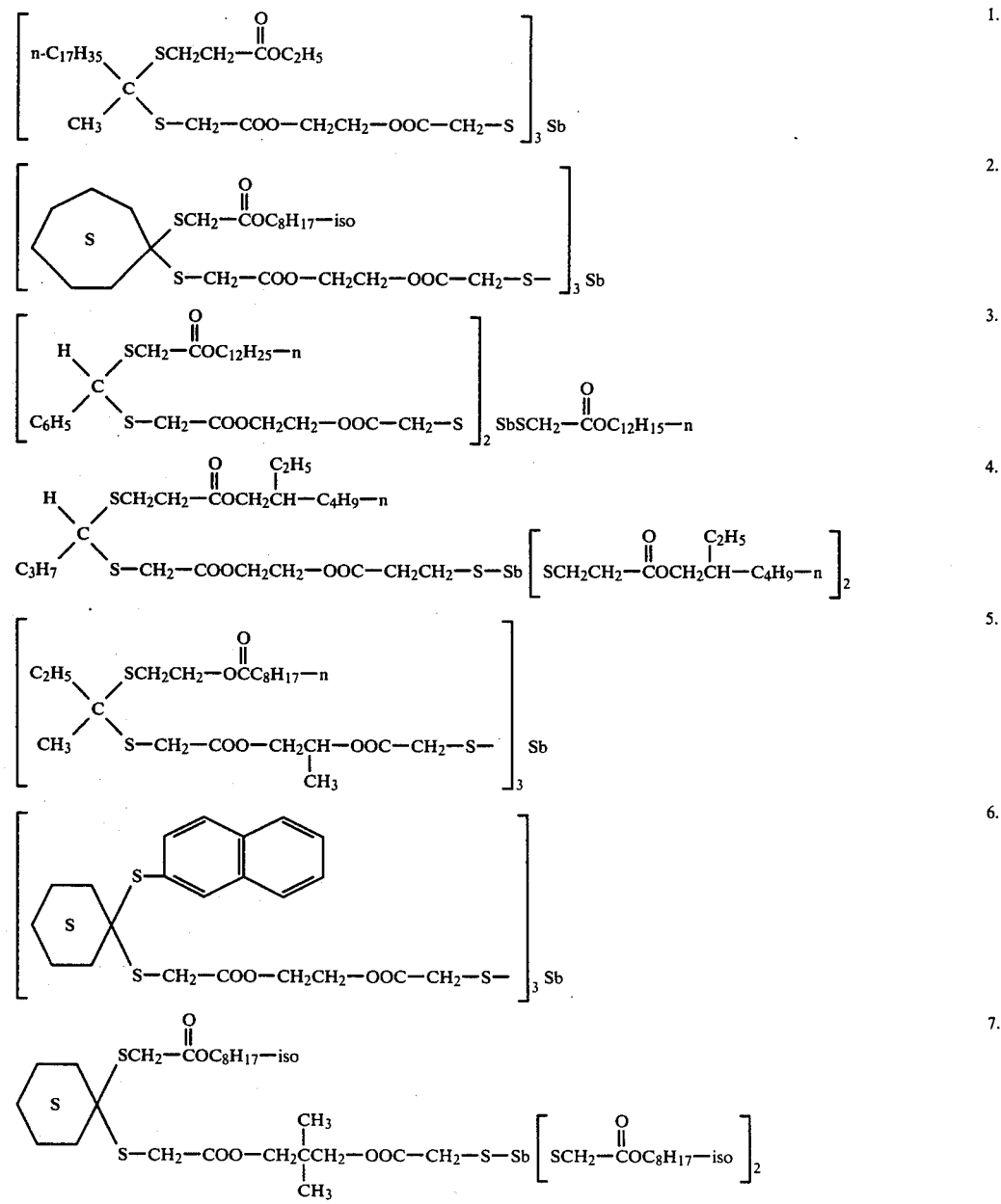

8.
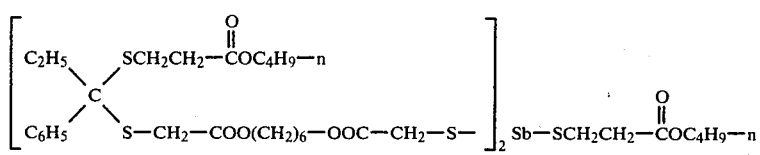
9.
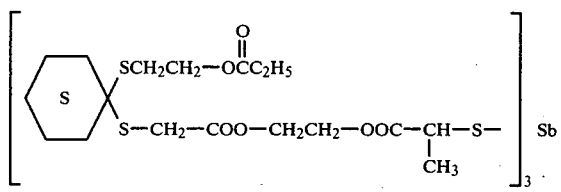
10.
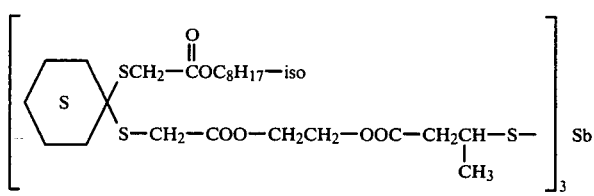
11.
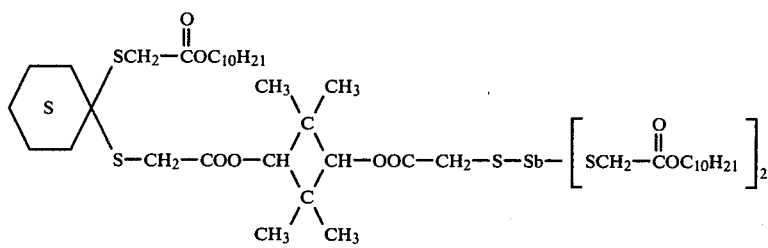
12.
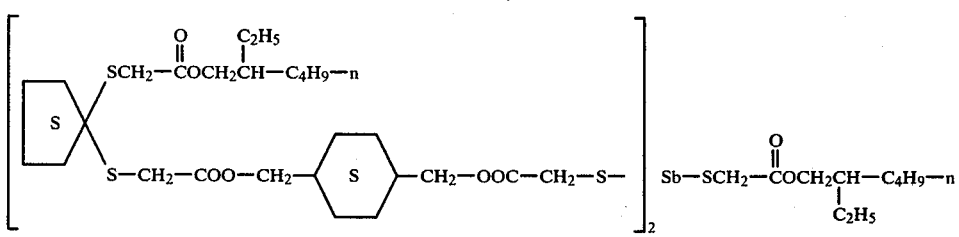
13.
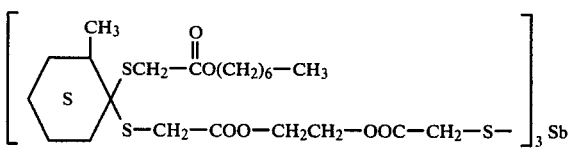
14.
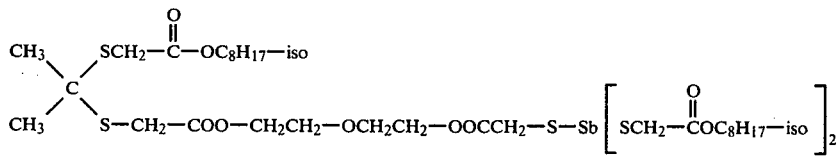
15.
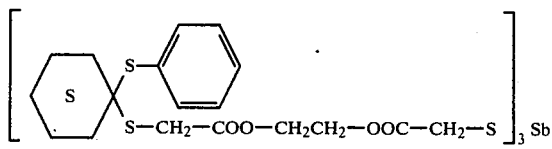
16.
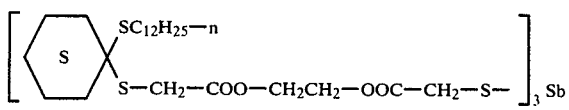

-continued

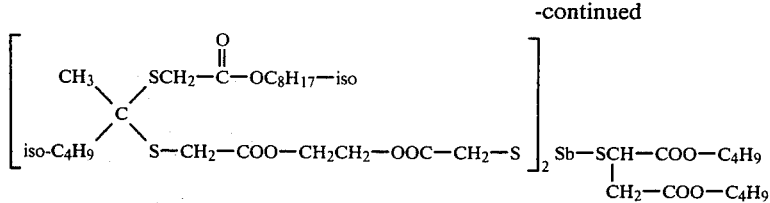
17.

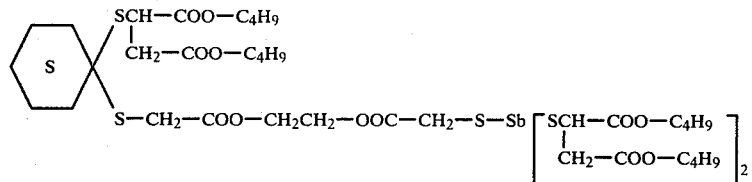
18.

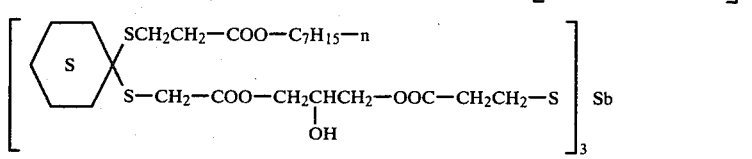
19.

The following Examples in the opinion of the inventor represent preferred embodiments of the antimony mercaptocarboxylic acid esters of the invention and of the process for preparing them:

EXAMPLE 1

Into a two-liter flask equipped with a Dean-Stark water trap, thermometer, stirrer, and reflux condenser were placed 225 g thioglycolic acid, 225 g cyclohexanone, 195 ml toluene, and 2.3 g p-toluene sulfonic acid (p-TSA). The mixture was heated to reflux temperature, initially 95° C. and rising to 120° C. during 105 minutes. During the reaction, a 45 ml aqueous lower layer was accumulated in the water trap, and titratable —SH (determined by titration with standardized iodine solution) decreased to 0.16%, indicating the consumption of 98.8% of the thioglycolic acid initially present by reaction with the cyclohexanone, forming the reaction product:

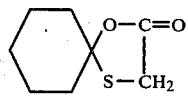

Isooctyl thioglycolate 472.5 g was added to the reaction vessel, and heating at the reflux temperature (125° to 135° C.) was continued for three hours. Analysis then showed 1.58% SH and an acid number of 88.4 (mg KOH/gram of sample), indicating 71% conversion of the cyclohexanone adduct to the dithiocycloalkylidene ester acid:

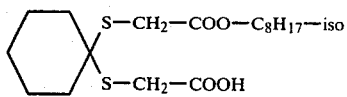

Ethylene glycol 146.3 g and 1.1 g p-TSA were then added, the water trap reinserted, and the mixture heated at reflux for four hours to decrease the acid number to 5.4, which represents about 92% conversion to the ester:

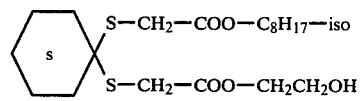

Thioglycolic acid 225 g was added, an esterification continued for six hours. To finish the operation, toluene was stripped to 130° C. and 15 mm, to give the desired ester, which analyzed 7.25% SH (calculated for the ester 6.68% SH) and an acid number of 23.6; these analyses represent an approximately 3.9% thioglycolic acid impurity in the final product, and an approximately 87.6% assay as the final ester:

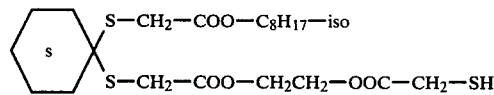

An antimony mercaptocarboxylate salt was prepared by heating to 70° C. a mixture of 180.3 g of this ester and 40.4 g of isooctyl thioglycolated, and adding in small portions 28.9 g antimony trioxide, while keeping the temperature in the 70° to 75° C. range. After complete addition of the antimony trioxide, the mixture was stirred one-half hour at 70° C., vacuum-stripped to remove reaction water at 15 mm pressure, and filtered, to give the desired antimony compound as a viscous oil having the composition:

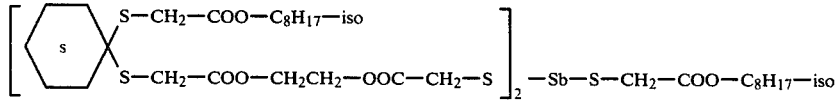

The product analyzed 8.94% Sb (by atomic absorption spectroscopy).

EXAMPLE 2

The ester

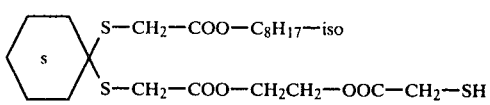

prepared as in Example 1 was converted to an antimony mercaptocarboxylate salt by heating to 70° C. a mixture of 109.2 g of this ester and 97.9 g of isooctyl thioglycolate, and adding in small portions 35 g antimony trioxide, while keeping the temperature in the 70° to 75° C. range. After complete addition of the antimony trioxide, the mixture was stirred one-half hour at 70° C., vacuum-stripped to remove reaction water at 15 mm pressure, and filtered to give the desired antimony compound as a viscous oil having the structure:

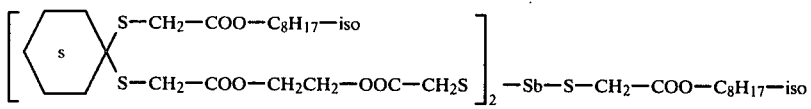

The product analyzed 11.8% Sb (by atomic absorption spectroscopy).

EXAMPLE 3

The ester

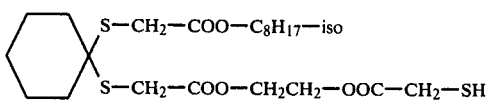

prepared as in Example 1 was converted to an antimony mercaptocarboxylate salt heating to 70° C. a mixture of 180.3 g of this ester (as the 75% toluene solution) and 400 g of isooctyl thioglycolate, adding in small portions 144 g antimony trioxide, while keeping the temperature in the 70° to 75° C. range. After complete addition of the antimony trioxide, the mixture was stirred one-half hour at 70° C., vacuum-stripped to remove reaction water at 15 mm pressure, and filtered to give the desired antimony compound as a viscous oil analyzing 12.64% Sb (by atomic absorption spectroscopy) and 10.74% SH (mercaptide sulfur), and having the structure:

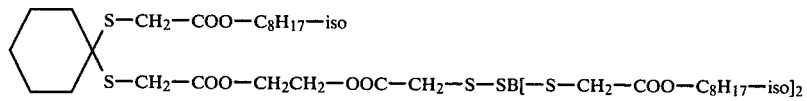

EXAMPLE 4

The ester

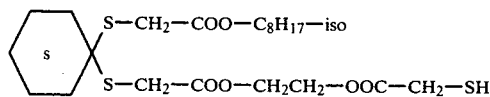

prepared as in Example 1 was converted to an antimony mercaptocarboxylate salt heating to 70° C. a mixture of 180.3 g of this ester (as the 75% toluene solution) and adding in small portions 24.2 g antimony trioxide, while keeping the temperature in the 70° to 75° C. range. After complete addition of the antimony trioxide, the mixture was stirred one-half hour at 70° C., vacuum-stripped to remove reaction water at 15 mm pressure, and filtered to give the desired antimony compound as a very viscous yellow oil having the structure:

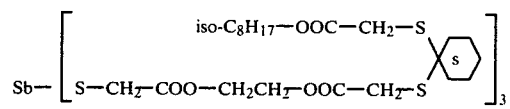

The product analyzed 7.59% Sb (by atomic absorption spectroscopy).

EXAMPLE 5

Into a two-liter flask equipped with a Dean-Stark water trap, thermometer, stirrer, and reflux condenser were weighed 100 g thioglycolic acid, 100 g methyl isobutyl ketone, 100 ml toluene, and 1 g p-toluene sulfonic acid (p-TSA). The mixture was heated to reflux temperature, initially 95° C. and rising to 120° C. during 105 minutes, while a 14 ml aqueous lower layer was accumulated in the water trap, and titratable —SH (determined by titration with standardized iodine solution) decreased to 2.3%; indicating the consumption of 81.6of the thioglycolic acid initially present by reaction with the ketone, forming the reaction product:

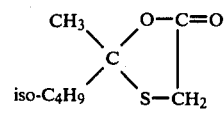

Isooctyl thioglycolate 204 g was added, and heating at the reflux temperature (125° to 135° C.) was continued for three hours. Analysis at this point showed 3.44% SH and an acid number of 96.3 (mg KOH/gram of sample), indicating conversion of the methyl isobutyl ketone adduct to the dithioalkylidene ester acid:

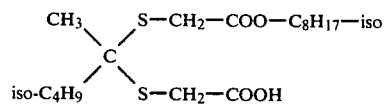

Ethylene glycol 62 g, 100 cc toluene and 0.5 g p-TSA were then added, the water trap reinserted, and the mixture heated at reflux for four hours to decrease the acid number to 6.0, which represents about 90% conversion to the ester:

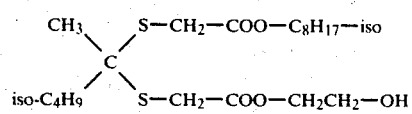

Thioglycolic acid 100 g was added to this toluene/ester solution, and esterification continued for six hours. To finish the operation, a portion of the toluene was stripped to 130° C. and 15 mm, to give an approximately 75% toluene solution of the desired ester, which analyzed 7.87% SH in agreement with the formula:

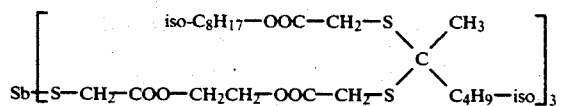

An antimony mercaptocarboxylate salt was prepared by heating to 70° C. a mixture of 180.3 g of this ester (as the 75% toluene solution) and adding in small portions 29 g antimony trioxide, while keeping the temprature in the 70° to 75° C. range. After complete addition of the antimony trioxide, the mixture was stirred one-half hour at 70° C., vacuum-stripped to remove reaction water at 15 mm pressure, and filtered to give the desired antimony compound as a very viscous yellow oil having the structure:

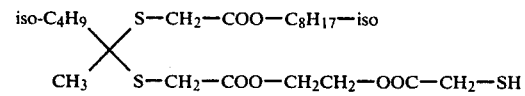

The product analyzed 10.9% Sb (by atomic absorption spectroscopy) and 10.8% SH (iodine-titratable mercaptide).

EXAMPLE 6

The ester

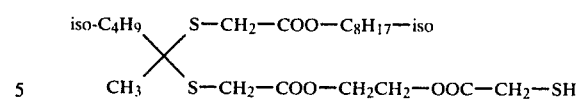

prepared as in Example 5 was converted to an antimony mercaptocarboxylate salt by heating to 70° C. a mixture of 100.4 g of this ester and 97.9 g of isooctyl thioglycolate, and adding in small portions 35 g antimony trioxide, while keeping the temperature in the 70° to 75° C. range. After complete addition of the antimony trioxide, the mixture was stirred one-half hour at 70° C., vacuum-stripped to remove reaction water at 15 mm pressure, and filtered to give the desired mixture of antimony compounds as a viscous oil having the structure:

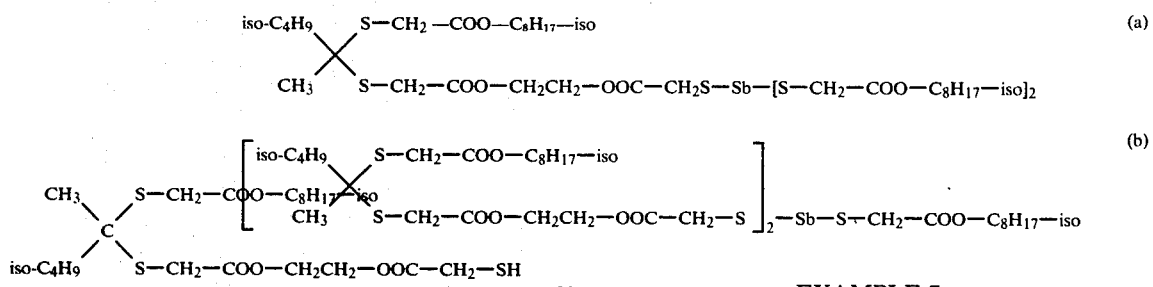

EXAMPLE 7

The ester prepared as in Example 5 was converted to an antimony mercaptocarboxylate salt heating to 70° C. a mixture of 166.1 g of this ester (as the 75% toluene solution) and 400 g of isooctyl thioglycolate, adding in small portions 144 g antimony trioxide, while keeping the temperature in the 70° to 75° C. range. After complete addition of the antimony trioxide, the mixture was stirred one-half hour at 70° C., vacuum-stripped to remove reaction water at 15 mm pressure, and filtered to give the desired mixture of antimony compounds as a viscous oil having the structure:

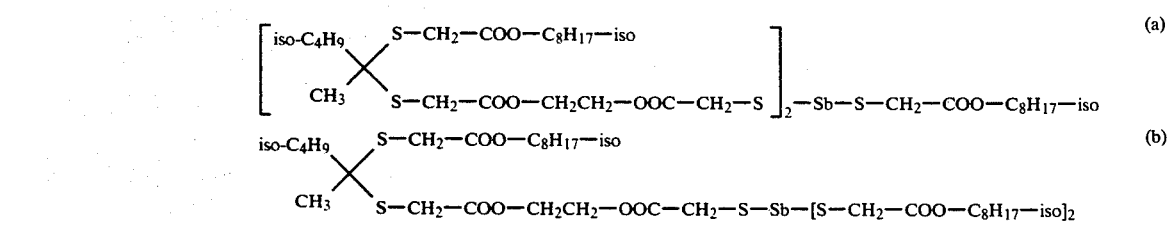

EXAMPLE 8

Into a two-liter flask equipped with a Dean-Stark water trap, thermometer, stirrer, and reflux condenser were weighed 100 g thioglycolic acid, 128 g 2-ethylhexanal, 100 ml toluene, and 1 g p-toluene sulfonic acid (p-TSA). The mixture was heated to reflux temperature, initially 95° C. and rising to 120° C. during 105 minutes, while at 17 ml aqueous lower layer was accumulated in the water trap, and titratable —SH (determined by titration with standardized iodine solution) decreased to 3.3%, indicating the consumption of the thioglycolic acid initially present by reaction with the 2-ethyl hexanal, forming the reaction product:

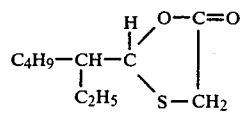

Isooctyl thioglycolate 204 g was added, and heating at the reflux temperature (125° to 135° C.) was continued for three hours. Analysis at this point showed much diminished SH and the appearance of an acid number indicating conversion of the 2-ethylhexanol adduct to the ester acid:

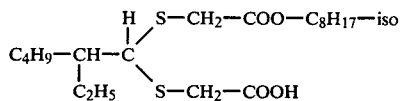

Ethylene glycol 62 g, 100 cc toluene and 0.5 g p-TSA were then added, the water trap reinserted, and the mixture heated at reflux for four hours to decrease the acid number which represents conversion to the ester:

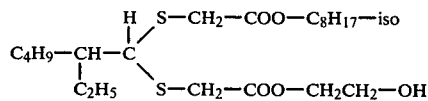

Thioglycolic acid 100 g was added to this toluene/ester solution, and esterification continued for six hours. To finish the operation, a portion of the toluene was stripped to 130° C. and 15 mm, to give an approximately 75% toluene solution of the desired ester, represented by the formula:

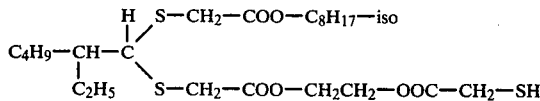

An antimony mercaptocarboxylate salt was prepared by heating to 70° C. a mixture of 192.8 g of this ester (as the 75% toluene solution) and adding in small portions 48 g antimony troxide, while keeping the temperature in the 70° to 75° C. range. After complete addition of the antimony trioxide, the mixture was stirred one-half hour at 70° C., vacuum-stripped to remove reaction water at 15 mm pressure, and filtered to give the desired antimony compound as a very viscous yellow oil having the structure:

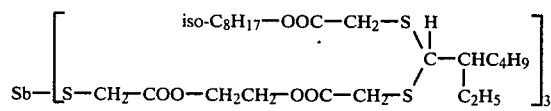

EXAMPLE 9

Into a two-liter flask equipped with a Dean-Stark water trap, thermometer, stirrer, and reflux condenser were weighed 106 g α-mercaptopropionic (thiolactic) acid, 100 g cyclohexanone, 100 ml toluene, and 1 g p-toluene sulfonic acid (p-TSA). The mixture was heated to reflux temperature, initially 95° C. and rising to 120° C. during 105 minutes, while a 17 ml aqueous lower layer was accumulated in the water trap, and titratable —SH (determined by titration with standardized iodine solution) decreased, indicating the consumption of the thiolactic acid initially present by reaction with the cyclohexanone, forming the reaction product:

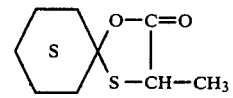

Isooctyl thioglycolate 204 g was added, and heating at the reflux temperature (125° to 135° C.) was continued for three hours. Analysis of this point showed SH and a positive acid number, indiciating conversion of the cyclohexanone adduct to the dithiocycloalkylidene ester acid:

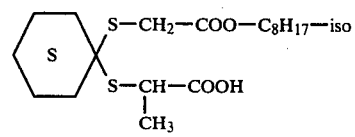

Ethylene glycol 62 g, 100 cc toluene and 0.5 g p-TSA were then added, the water trap reinserted, and the mixture heated at reflux for four hours to convert to the ester:

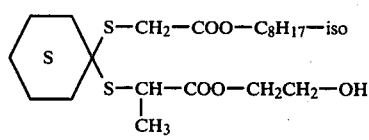

Thioglycolic acid 100 g was added to this toluene/ester solution, and esterification continued for six hours. To finish the operation, a portion of the toluene was stripped to 130° C. and 15 mm, to give an approximately 75% toluene solution of the desired ester, represented by the formula:

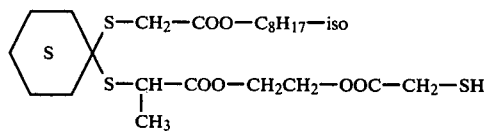

An antimony mercaptocarboxylate salt was prepared by heating to 70° C. a mixture of 180.3 g of this ester (as the 75% toluene solution) and adding in small portions 38 g antimony trioxide, while keeping the temperature in the 70° to 75° C. range. After complete addition of the antimony trioxide, the mixture was stirred one-half hour at 70° C., vacuum-stripped to remove reaction water at 15 mm pressure, and filtered to give the desired antimony compound as a very viscous yellow oil having the structure:

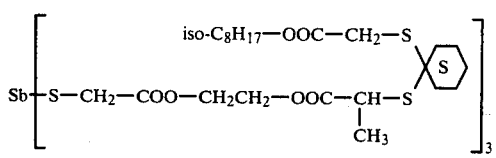

The product analyzed 14.5% Sb (by atomic absorption spectroscopy).

EXAMPLE 10

A toluene solution containing about one mole of the ester

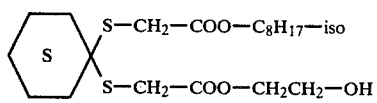

along with 100 cc toluene and 0.5 g p-toluene sulfonic acid was treated with 106 g β-mercaptopropionic acid while being stirred and heated with a Dean-Stark water trap and reflux condenser. The esterification was continued for six hours. To finish the operation, a portion of the toluene was stripped to 130° C. and 15 mm, to give an approximately 75% toluene solution of the desired ester, which analyzed 7.04% SH in reasonable agreement with the formula:

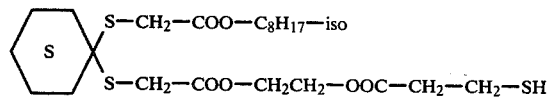

An antimony mercaptocarboxylate salt was prepared by heating to 70° C. a mixture of 184.1 g of this ester (as the 75% toluene solution) and adding in small portions 48 g antimony trioxide, while keeping the temperature in the 70° to 75° C. range. After complete addition of the antimony trioxide, the mixture was stirred one-half hour at 70° C., vacuum-stripped to remove reaction water at 15 mm pressure, and filtered to give the desired antimony compound as a very viscous yellow oil having the structure:

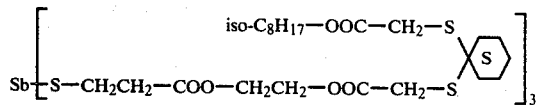

EXAMPLE 11

Into a two-liter flask equipped with a Dean-Stark water trap, thermometer, stirrer, and reflux condenser were weighed 100 g thioglycolic acid, 100 g cyclohexanone, and 100 ml toluene. The mixture was heated to reflux temperature, initially 95° C. and rising to 120° C. during 105 minutes, while a 45 ml aqueous lower layer was accumulated in the water trap, and titratable—SH (determined by titration with standardized iodine solution) decrease to 0.16%, indicating the consumption of 98.8% of the thioglycolic acid initially present by reaction with cyclohexane, forming the reaction product:

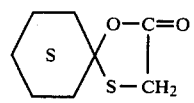

Isooctyl thioglycolate 204 g was added, and heating at the reflux temperature (125° to 135° C.) was continued for three hours. Analysis at this point showed 1.58% SH and an acid number of 88.4 (mg KOH/gram of sample), indicating 71% conversion of the cyclohexanone adduct to the dithiocycloalkylidene ester acid:

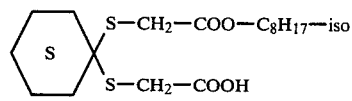

Ethylene glycol 62 g, 100 cc toluene 0.5 g p-TSA were then added, the water trap reinserted, and the mixture heated at reflux for four hours to decrease the acid number to 5.4, which represents about 92% conversion to the ester:

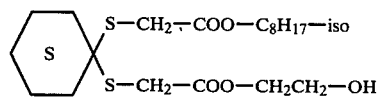

Thioglycolic acid 100 g was added to this toluene/ester solution, and esterification continued for six hours. To finish the operation, a portion of the toluene was stripped to 130° C. and 15 mm, to give an approximately 70% toluene solution of the desired ester, which analyzed 7.50% SH in the final product and an approximately 90% assay as the final ester:

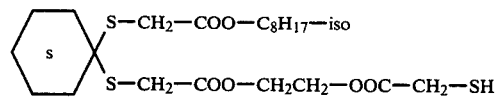

An antimony mercaptocarboxylate salt was prepared by heating to 70° C. a mixture of 180 g of this ester (as the 70% toluene solution) and adding in small portions 24 g antimony trioxide, while keeping the temperature in the 70° to 75° C. range. After complete addition of the antimony trioxide, the mixture was stirred one-half hour at 70° C. vacuum-stripped to remove reaction water at 15 mm pressure, and filtered to give the desired antimony compound as a very viscous yellow oil having the structure:

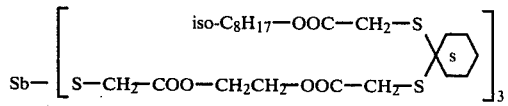

EXAMPLE 12

Into a solution of 44 g (1 mole) acetaldehyde in 200 ml toluene 92 g (1 mole) thioglycolic acid was added, and the mixture stirred for two hours at room temperature. The mixture was then refluxed for six hours, the water formed in the reaction being continuously removed by azeotropic distillation. The reaction mixture was then washed with a saturated sodium bicarbonate solution, and the washed product distilled under vacuum to give a 40% yield of a pale yellow liquid of b.p. 70° to 72° C. at 5 mm. The product was 2-methyl-1-oxa-3-thiolan-5-one represented by the formula:

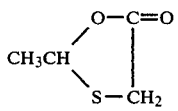

Into a solution of 118 g (1 mole) of this oxathiolanone and 200 ml benzene, 204 g (1 mole) isooctyl thioglycolate was added and the mixture was refluxed for six hours at 125° to 130° C. Analysis indicated that the acid number had risen from 1.2 to 95 mg KOH/g, indicating 55% conversion of the oxathiolanone to the dithioethylidene ester acid:

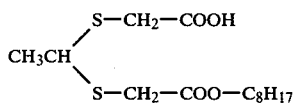

This acid on heating with an equimolar amount of ethylene glycol and 0.4% by weight of toluene sulfonic acid catalyst gave the hydroxy ester:

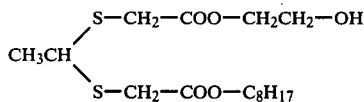

which was esterified with thioglycolic acid under the conditions of Example 9 to give the mercaptoester

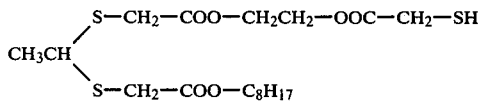

By heating and stirring together one molar proportion of this mercaptoester and one-sixth molar proportion of antimony trioxide at 75° to 95° C. for four hours with vacuum applied to remove reaction water, there was obtained the oily and viscous antimony mercaptocarboxylic ester:

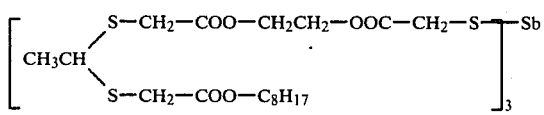

EXAMPLE 13

Under conditions like those of Example 12 above, from 72 g (1 mole) n-butyraldehyde, 200 cc toluene, and 92 g (1 mole) thioglycolic acid, there was obtained a 55% yield of 2-n-propyl-1-oxa-3-thiolan-5-one having the formula:

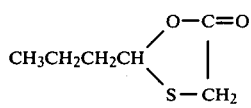

which was a pale yellow liquid with a b.p. 74° to 75° C. at 5 mm.

Into a solution of 146 g (1 mole) of this oxathiolanone and 200 ml toluene, 216 g (1 mole) isooctyl betamercaptopropionate was added and the mixture refluxed for six hours at 125° to 130° C. Analysis indicated a 60% yield of the dithiobutylidene ester acid:

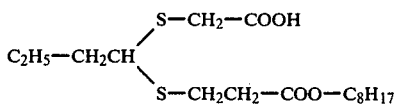

The above acid on heating with an equimolar amount of ethylene glycol and 0.4% by weight of toluene sulfonic acid catalyst gave the hydroxy ester:

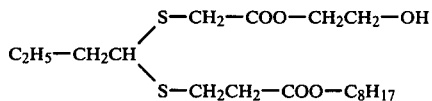

which was esterified with 3-mercaptopropionic acid under the conditions of Example 10 to give the 3-mercaptopropionic ester:

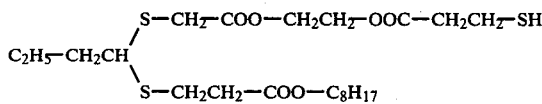

By heating and stirring together one-third molar proportion of this mercaptopropionate ester with two-thirds molar proportion of n-hexyl-3-mercaptopropionic and one-sixth molar proportion of antimony trioxide as in the previous Example, there was obtained the mobile liquid antimony mercaptocarboxylic acid ester:

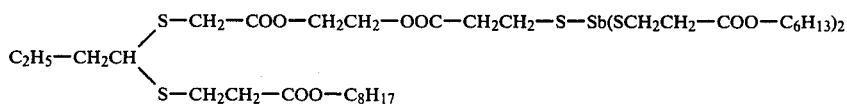

EXAMPLE 14

A mixture of methyl isopropyl ketone 86 g (1 mole), thioglycolic acid 92 g (1 mole), 200 ml toluene and 1 g p-toluene sulfonic acid was heated under reflux until 18 ml water was obtained during about 5½ hours. The mixture was washed several times with saturated sodium bicarbonate solution and distilled to give a 75% yield of 2-methyl-2-isopropyl-1-oxa-3-thiolan-5-one as a colorless liquid of b.p. 101° to 102° C./11 mm, having the formula:

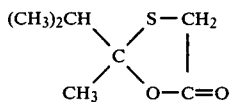

160 g (1 mole) of the above oxathiolanone was added to a mixture of 200 ml toluene and 204 g (1 mole) isooctyl thioglycolate and refluxed for six hours. There was obtained a pale yellow oily liquid as an 80% yield of the product represented by the formula:

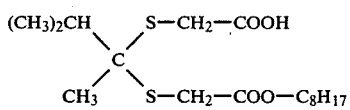

Equimolar amounts of this product and ethylene glycol on heating in the presence of two drops methane sulfonic acid produced the hydroxyester:

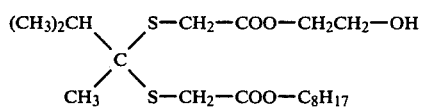

which was esterified with thioglycolic acid under the conditions of Example 9 to give the thioglycolic acid ester:

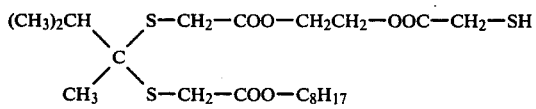

By heating and stirring together two-thirds molar proportion of this mercaptoester and one-third molar proportion of cyclohexyl thioglycolate and one-sixth molar proportion of antimony trioxide, there was obtained the oily and viscous antimony mercaptoester represented by the formula:

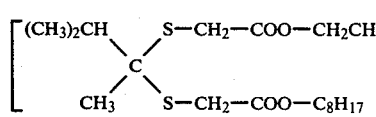

EXAMPLE 15

A solution of 106 g (1 mole) benzaldehyde and 200 ml benzene, 92 g (1 mole) thioglycolic acid, and 1.25 g toluene sulfonic acid as catalyst was refluxed for eight hours. The product was washed with saturated sodium bicarbonate solution, separated and stripped to remove the benzene. The crude product obtained in 60% yield was recrystallized from n-hexane to give very pale yellow crystals having m.p. 57° to 58° C. of 2-phenyl-1-oxa-3-thiolan-5-one represented by the formula:

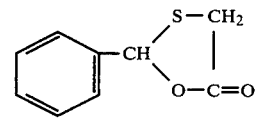

To 90 g (0.5 mole) of this oxathiolanone was added 200 ml benzene and 102 g (0.5 mole) isooctyl thioglycolate. The mixture was refluxed for seven hours, water washed and stripped and analyzed to contain an 80% yield of the dithiobenzylidene ester acid of the formula:

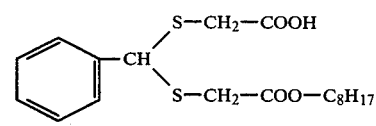

The above ester acid on heating with 100% excess over an equimolar amount of 1,4-butanediol and toluene sulfonic acid catalyst gave the hydroxyester:

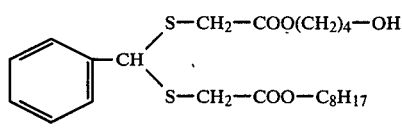

which was washed to remove unconverted butanediol and esterified with thioglycolic acid under the conditions of Example 9 to give the mercaptoester:

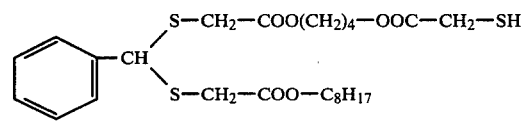

which in turn was converted to an antimony mercaptocarboxylic ester by heating with one-sixth molar proportion of antimony trioxide as described above. The antimony mercaptoester was represented by the formula:

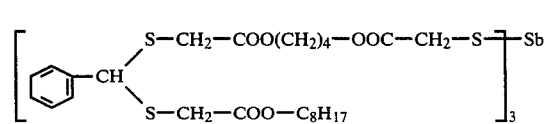

EXAMPLE 16

2,2-Pentamethylene-1-oxa-3-thiolan-5-one 172 g (1 mole) prepared as described in Example 1 was heated with 100 ml toluene, 183 g (1.1 mole) p-t-butylthiophenol, and 1 g toluene sulfonic acid at 135° to 140° C. for nine hours. Diminution in the SH analysis and increase in the acid number demonstrated the formation in approximately 50% yield of the t-butylphenylthiocyclohexylidene acid having the formula:

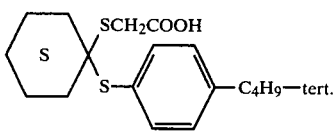

t-Butylphenylthiocyclohexylidene thioacetic acid prepared as above was heated and stirred with an equimolar amount of ethylene glycol and 0.4% by weight of toluene sulfonic acid catalyst to give the hydroxyester:

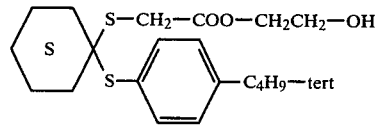

which was esterified with thioglycolic acid under the conditions of Example 9 to give the thioglycolate ester:

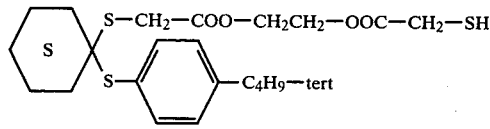

One molar proportion of this ester and one-sixth molar proportion of antimony trioxide boiled in toluene to remove reaction water by azeotropic distillation gave the antimony mercaptocarboxylic acid ester:

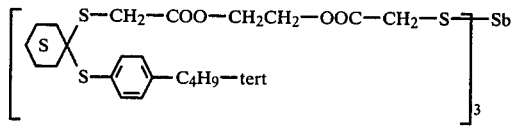

EXAMPLE 17

To a solution containing approximately one mole of 2,2-pentamethylene-1-oxa-3-thiolan-5-one and 100 cc toluene, prepared as in Example 4, there was added 216 g (1 mole) isooctyl β-mercaptopropionate. Heating at the reflux temperature (125° to 135° C.) was continued for three hours. Analysis at this point showed 1.50% SH and an acid number of 80.0 (mg KOH/gram of sample), indicating 73% conversion of the cyclohexanone adduct to the dithiobutylidene ester acid:

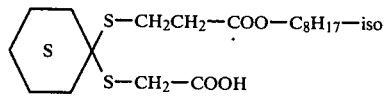

Ethylene glycol 62 g, 100 cc toluene and 0.5 g p-TSA were then added, the water trap reinserted, and the mixture heated at reflux for four hours to decrease the acid number to 6.2, which represents about 90% conversion to the ester:

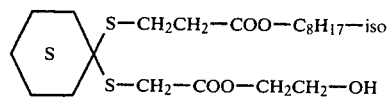

Thioglycolic acid 100 g was added to this toluene/ester solution, and esterification continued for six hours. To finish the operation, a portion of the toluene was stripped to 130° C. and 15 mm, to give an approximately 75% toluene solution of the desired ester, which analyzed 5.38% SH and an acid number of 20.6; these analyses represent an approximately 3.0% thioglycolic acid impurity in the final product and an approximately 88% assay as the final ester:

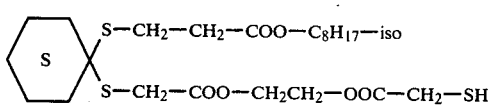

An antimony mercaptocarboxylate salt was prepared by heating to 70° C. a mixture of 180 g of this ester (as the 75% toluene solution) and adding in small portions 48 g antimony trioxide, while keeping the temperature in the 70° to 75° C. range. After complete addition of the antimony trioxide, the mixture was stirred one-half hour at 70° C., vacuum-stripped to remove reaction water at 15 mm pressure, and filtered to give the desired antimony compound as a very viscous yellow oil having the structure:

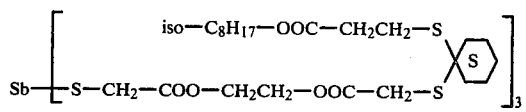

EXAMPLE 18

The ester

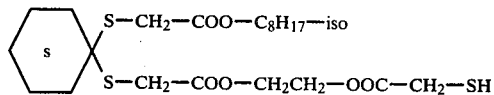

prepared as in Example 1 was converted to a lithium mercaptocarboxylate salt by heating to 50° C. a mixture of 180.3 g of this ester (as the 75%toluene solution) and adding in small portions 15.8 g lithium hydroxide monohydrate while keeping the temperature in the 55° to 70° C. range. After complete addition of the lithium base, the mixture was stirred one-half hour at 75° C., vacuum-stripped to remove reaction water at 15 mm pressure, and filtered to give the desired lithium compound as a slightly viscous yellow oil having the structure:

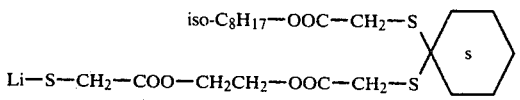

EXAMPLE 19

The ester

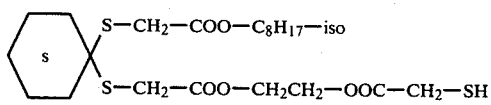

prepared as in Example 1 was converted to a lead mercaptocarboxylate salt by heating to 40° C. a mixture of 180.3 g of this ester (as the 75% toluene solution) and adding in small portions 320 g of 20% aqueous lead acetate solution while keeping the temperature in the 40° to 45° C. range. After complete addition of the lead acetate, the mixture was stirred one-half hour at 45° C., and the layers allowed to separate. After removing the aqueous phase, the toluene layer was evaporated at 15 mm pressure, and filtered to give the desired lead compound as a very viscous yellow oil having the structure:

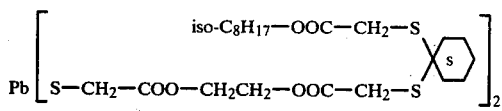

EXAMPLE 20

The ester

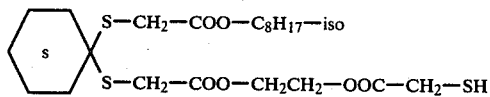

prepared as in Example 1 was converted to a barium mercaptocarboxylate salt by heating to 40° C. a mixture of 180.3 g of this ester (as the 75% toluene solution) and adding in small portion 60 g barium hydroxide octahydrate and 100 ml water while keeping the temperature in the 50° to 60° C. range. After completion addition of the barium hydroxide, the mixture was stirred one-half hour at 65° C., the layers separated and the toluene solution vacuum-stripped to remove water and toluene at 15 mm pressure, and filtered to give the desired barium compound as a very viscous yellow oil having the structure:

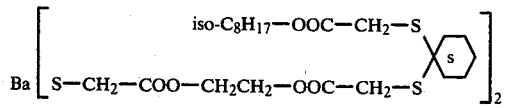

EXAMPLE 21

The ester

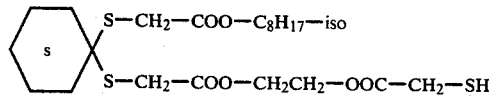

prepared as in Example 1 was converted to a magnesium mercaptocarboxylate salt by heating to 90° C. a mixture of 180.3 g of this ester (as the 75% toluene solution) and adding in small portion 7.3 g magnesium oxide, while keeping the temperature in the 90° to 100° C. range. After complete addition of the magnesium oxide, the mixture was stirring one-half hour at 100° C., vacuum-stripped to remove reaction water at 15 mm pressure, and filtered to give the desired magnesium compound as a very viscous yellow oil having the structure:

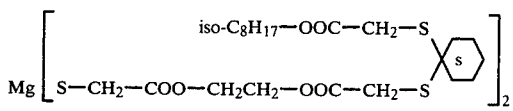

EXAMPLE 22

The ester

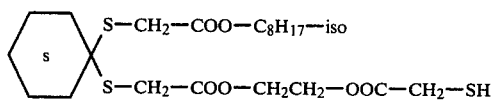

prepared as in Example 1 was converted to a cadmium mercaptocarboxylate salt by heating to 50° C. a mixture of 180.3 g of this ester (as the 75% toluene solution) and adding in small portions 220 g 15% aqueous cadmium acetate while keeping the temperature in the 50° to 60° C. range. After complete addition of the cadmium acetate, the mixture was stirred one-half hour at 60° C., and allowed to separate into two layers. The aqueous phase was removed and the toluene phase evaporated at 15 mm pressure, and filtered to give the desired cadmium compound as a very viscous yellow oil having the structure:

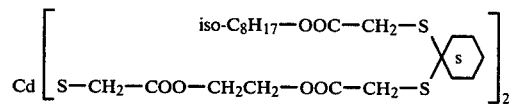

EXAMPLE 23

The ester

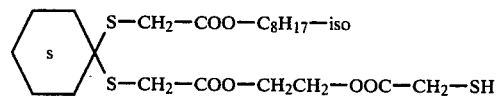

prepared as in Example 1 was converted to a zinc mercaptocarboxylate salt by heating to 50° C. a mixture of 180.3 g of this ester (as the 75% toluene solution) and adding in small portions 390 g 9% aqueous zinc acetate while keeping the temperature in the 50° to 60° C. range. After complete addition of the zinc acetate, the mixture was stirred one-half hour at 60° C., and allowed to separate into two layers. The aqueous phase was removed and the toluene phase evaporated at 15 mm pressure, and filtered to give the desired zinc compound as a very viscous yellow oil having the structure:

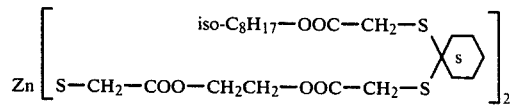

EXAMPLE 24

The ester

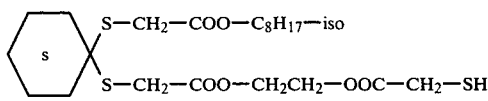

prepared as in Example 1 was converted to a calcium mercaptocarboxylate salt by heating to 45° C. a mixture of 180.3 g of this ester (as the 75% toluene solution) and adding in small portions 165 g 12% aqueous calcium hydrosulfide solution while keeping the temperature in the 40° to 45° C. range. After complete addition of the calcium hydrosulfide, the mixture was stirred one and one-half hours at 40° C. while blowing with nitrogen to displace hydrogen sulfide into a container of lime slurry, thus regenerating calcium hydrosulfide. When no more $H_2S$ was evolved, the mixture was allowed to separate into two layers and the aqueous phase was removed. The toluene solution of the product was evaporated under reduced pressure to give the desired calcium compound as a very viscous yellow oil having the structure:

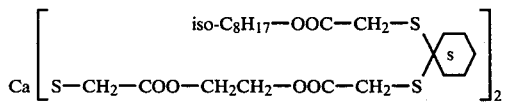

EXAMPLE 25

The ester

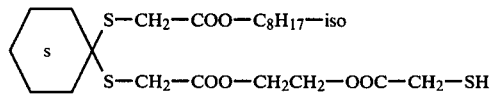

prepared as in Example 1 was converted to a n-octyltin tri-(mercaptocarboxylate) salt by heating to 40° C. a mixture of 180.3 g of this ester (as the 75% toluene solution) with 43 g n-octyltin trichloride and adding dropwise a solution of 7.1 g KOH and 63 ml water while keeping the temperature in the 45° to 55° C. range. After complete addition of the potassium hydroxide, the mixture was stirred one-half hour at 60° C., the layers separated, and the toluene layer vacuum-stripped to remove water and toluene at 15 mm pressure, and filtered to give the desired n-octyltin compound as a viscous yellow oil having the structure:

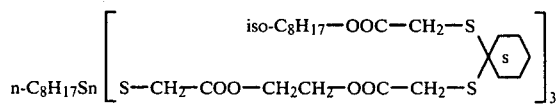

EXAMPLE 26

The ester

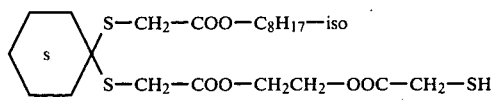

prepared as in Example 1 was converted to a dibutyltin mercaptocarboxylate salt heating to 50° C. a mixture of 180.3 g of this ester (as the 75% toluene solution) and adding in small portions 49 g di-n-butyltin oxide while keeping the temperature in the 50° to 55° C. range. After complete addition of the oxide, the mixture was stirred one-half hour at 55° C., vacuum-stripped to remove reaction water and toluene at 15 mm pressure, and filtered to give the desired dibutyltin compound as a viscous yellow oil having the structure:

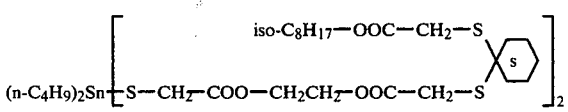

EXAMPLE 27

One mole of the cycloakylidene dithiocarboxylic ester acid prepared as in Example 1 was neutralized with sodium bicarbonate to form the sodium salt having the structure:

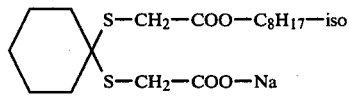

The above was diluted with 1000 ml benzene and mixed with one-half mole (95 g) stannous chloride to give a benzene solution of the stannous salt of the formula:

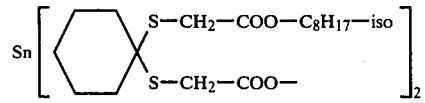

The mixture was washed with water to remove salt and the organic layer was separated. The benzene was stripped off to give a viscous pale yellow oil solution which analyzed 9.85% tin (theoretical tin content 10.86%).

EXAMPLES 28 to 32

The cyclohexylidene dithiocarboxylic ester acid prepared as in Example 1 was neutralized with sodium bicarbonate reacted under the conditions shown in Example 27 for stannous chloride with one-half molar proportion of each of the metal chlorides shown in the Table below. A work-up procedure as in Example 27 gave the oily metal salts of the ester acid as shown:

TABLE 1

| Example No. | Metal Chloride | Cyclohexylidene dithiocarboxylic ester acid salt | Theoretical % metal | Actual % metal |
|---|---|---|---|---|
| 28 | $MgCl_2$ | $\left[\underset{S-CH_2-COO-}{\overset{S-CH_2-COO-C_8H_{17}-iso}{\bigcirc\!\!\!\!\times}}\right]_2 Mg$ | 2.43 Mg | 2.0 Mg |
| 29 | $CaCl_2$ | $\left[\underset{S-CH_2-COO-}{\overset{S-CH_2-COO-C_8H_{17}-iso}{\bigcirc\!\!\!\!\times}}\right]_2 Ca$ | 3.96 Ca | 3.12 Ca |
| 30 | $CdCl_2$ | $\left[\underset{S-CH_2-COO-}{\overset{S-CH_2-COO-C_8H_{17}-iso}{\bigcirc\!\!\!\!\times}}\right]_2 Cd$ | 10.8 Cd | 9.6 Cd |
| 31 | $SrCl_2$ | $\left[\underset{S-CH_2-COO-}{\overset{S-CH_2-COO-C_8H_{17}-iso}{\bigcirc\!\!\!\!\times}}\right]_2 Sr$ | 8.24 Sr | 7.85 Sr |
| 32 | $ZnCl_2$ | $\left[\underset{CH_2-COO-}{\overset{S-CH_2-COO-C_8H_{17}-iso}{\bigcirc\!\!\!\!\times}}\right]_2 Zn$ | 6.21 Zn | 5.95 Zn |

EXAMPLE 33

The preparation of a zinc salt of the cyclohexylidene dithiocarboxylic ester acid as in Example 32 was repeated using without isolation the ester acid made as in Example 1 where the conversion of the 2,2-pentamethylene-1,3-oxathiolan-5-one to the ester acid was approximately 71% based on the 88.4 acid number of the mixture. Accordingly, 10.1 g of zinc chloride was used for 100 g of the reaction mixture.

EXAMPLE 34

A dithiocycloalkylidene ester acid organothin salt was prepared by bringing together at 65° C. 484 g of the cyclohexylidene dithiocarboxylic ester acid prepared as in Example 1 and 125 g di-n-butyltin oxide, heating for one hour at this temperature to dissolved and react the oxide, and removing reaction water by application of vacuum for twenty minutes at 70° to 80° C. The product was obtained in the form of a viscous yellow oil of the structure:

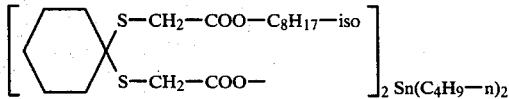

This invention further provides polyvinyl chloride resin compositions suitable for extrusion in multi-screw extruders or calendering and having an enhanced resistance to the development of early discoloration when heated at 375° F., comprising a polyvinyl chloride resin, an antimony mercaptocarboxylic acid ester of the invention, and optionally a mercaptocarboxylic acid ester, and/or an ortho-dihydric phenol, and/or an organic phosphite, and/or an alkaline earth metal carboxylate or epoxidized triglyceride ester, or both. Preferred for use in such polyvinyl chloride resin compositions are blends of the antimony mercaptocarboxylic acid ester and ortho-dihydric phenol which have been heated at an elevated temperature of at least about 50° C. for at least fifteen minutes. To such reaction products there can also be added an alkaline earth metal carboxylate and/or epoxidized triglyceride ester.

Accordingly, the stabilizer system in accordance with the invention can optionally include a mercaptocarboxylic acid ester having the formula:

[R₁COOR₂] SH wherein:

R₁ and R₂ are hydrocarbon radicals selected from the group consisting of aliphatic, cycloaliphatic and aromatic hydrocarbon radicals, the aliphatic radicals having from one to about twenty carbon atoms, the cycloaliphatic radicals having from three to about twenty carbon atoms, and the aromatic radicals having from six to about twenty carbon atoms.

The SH group can be attached to either $R_1$ or to $R_2$. When the SH is attached to $R_1$, the compounds are esters of mercaptocarboxylic acids. When the SH is attached to $R_2$, the compounds are carboxylic acid esters of mercaptoalcohols. Both are referred to generically herein by the term "mercaptocarboxylic acid esters", which therefore encompasses both.

Exemplary aliphatic $R_1$ and $R_2$ radicals include methyl, ethyl, propyl, secondary butyl, N-butyl, tertiary butyl, isobutyl, octyl, isooctyl, 2-ethylhexyl, tert-octyl, decyl, lauryl, myristyl, stearyl and eicosyl.

Exemplary cycloaliphatic groups include cyclopropyl, cyclobutyl, cyclopentyl, cyclohexyl, cycloheptyl, cyclooctyl, and cyclododecyl, and hydrocarbon-substituted such cycloaliphatic radicals, including methyl cycloheptyl, ethyl cyclopentyl, nonyl cyclohexyl, dibutyl cyclohexyl, methyl cycloheptyl and ethyl cyclooctyl.

Exemplary aromatic hydrocarbon radicals include phenyl, xylyl, tolyl, mesityl, ethyl phenyl, diethyl phenyl, nonyl phenyl, dodecyl phenyl, naphthyl, anthracyl, phenanthryl, alpha-methyl naphthyl, and beta-methyl naphthyl.

The mercaptocarboxylic acid esters can be derived from any of the mono- or poly-α- and β-mercaptocarboxylic acids and monohydric and dihydric alcohols and polyols referred to above at pages 29 and 30, in connection with the antimony mercaptocarboxylic acid esters. The mercaptocarboxylic acids and esterifying alcohols in the antimony mercaptocarboxylic acid esters and the mercaptocarboxylic acid esters can be the same or different.

The stabilizer system in accordance with the invention can also include an ortho-dihydric phenol. The effectiveness of this class of the ortho-dihydric phenols is unique, and not displayed by its isomers, the metal and para dihydric phenols, such as hydroquinone and resorcinol.

The class of ortho-dihydric phenols has the following general formula:

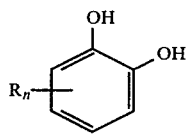

where:
R is selected from the group consisting of hydroxyl, alkyl, cycloalkyl, aryl, alkoxy, aryloxy, alkenyl, carboxylalkyl, carboxyaryl, acyl, aryl, alkenyloxy, hydroxyalkyl, hydroxyaryl, alkoxyaryl, and alkoxyalkyl having from one to about twelve carbon atoms; and
n is an integer from zero to four.

Exemplary ortho dihydric phenols include catechol (which is preferred because of its cost and effectiveness), alkyl catechols such as p-t-butyl-catechol, p-methyl-catechol, m-ethyl-catechol, alkoxy catechols such as p-methoxy catechol, p-propoxy-catechol, p-hexoxy-catechol, cycloalkyl catechols such as p-cyclohexyl-catechol, halogenated catechols such as m-chloro-catechol, p-chloro-catechol, p-bromo-catechol, polynuclear catechols such as p-phenyl catechol, α,β-dihydroxy naphthyl catechol, 2,2-di-(4,5-dihydroxyphenyl) propane and bis-(4,5-dihydroxy phenyl) methane.

The stabilizer mixtures of the invention can also include an organic triphosphite and/or an acid phosphite. Such combinations are complementary, and may impart an enhanced resistance of the polymer to deterioration when exposed to light and/or heat.

A variety of organic triphosphites and acid phosphites can be employed, of which the following are exemplary.

The organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophosphites.

The organic triphosphites in which the radicals are monovalent radicals can be defined by the formula:

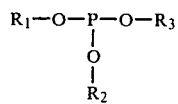

in which $R_1$, $R_2$ and $R_3$ are selected from the group consisting of alkyl, alkenyl, aryl, alkaryl, aralkyl, and cycloalkyl groups having from one to about thirty carbon atoms.

The acid phosphites are defined by the same formula, but one or two of $R_1$, $R_2$ and $R_3$ is hydrogen or a cation of a metal or ammonium.

Also included are the organic triphosphites having a bivalent organic radical forming a heterocyclic ring with the phosphorus of the type:

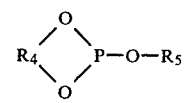

in which $R_4$ is a bivalent organic radical selected from the group consisting of alkylene, arylene, aralkylene, alkarylene and cycloalkylene radicals having from two to about thirty carbon atoms, and $R_5$ is a monovalent organic radical as defined above in the case of $R_1$, $R_2$ and $R_3$.

$R_5$ is hydrogen or a cation, in the case of the acid phosphites.

Also useful organic triphosphites are mixed heterocyclic-open chain phosphites of the type:

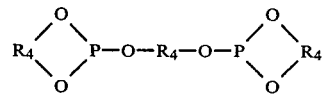

More complex triphosphites are formed from trivalent organic radicals, of the type:

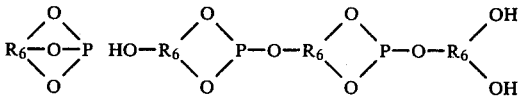

in which $R_6$ is a trivalent organic radical of any of the types of $R_1$ to $R_5$, inclusive, as defined above.

A particularly useful class of complex triphosphites are the tetraoxadiphosphaspiro undecanes of the formula:

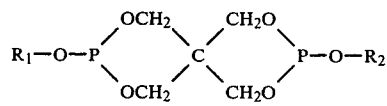

where $R_1$ and $R_2$ are selected from the group consisting of aryl, alkyl, aryloxyethyl, alkyloxyethyl, aryloxyethoxyethyl, alkyloxyethoxyethyl and alkyloxypolyethoxyethyl having from about one to about thirty carbon atoms.

In the case of the acid phosphites, one or both of $R_1$ and $R_2$ is also hydrogen or a cation.

An especially preferred class of organic triphosphites and acid phosphites have a bicyclic aromatic group attached to phosphorus through oxygen, with no or one or more phenolic hydroxyl groups on either or both of the aromatic rings. These phosphites are characterized by the formula:

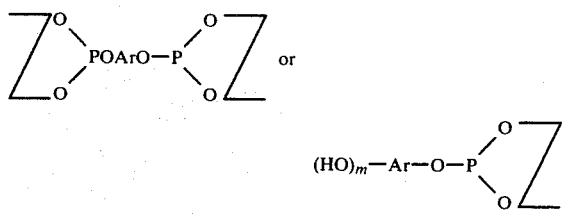

in which Ar is a mono or bicyclic aromatic nucleus and m is an integer of from 0 to about 5. is one or a plurality of organic radicals as defined above for $R_1$ to $R_6$, taken singly or together in sufficient number to satisfy the valences of the two phosphite oxygen atoms.

One or both radicals is also hydrogen, in the case of the acid phosphites, and can include additional bicyclic aromatic groups of the type $(HO)_m$—Ar.

The cation in the case of acid phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, diphenyl mono-2-ethylhexyl phosphite, di-isooctyl monotolyl phosphite, tri-2-ethylhexyl phosphite, phenyl dicyclohexyl phosphite, phenyl diethyl phosphite, triphenyl phosphite, tricresyl phosphite, tri(dimethylphenyl)phosphite, trioctadecyl phosphite, triisooctyl phosphite, tridodecyl phosphite, isooctyl diphenyl phosphite, diisooctyl phenyl phosphite, tri(t-octylphenyl)phosphite, tri(t-nonylphenyl)phosphite, benzyl methyl isopropyl phosphite, butyl dicresyl phosphite, isooctyl di(octylphenyl)phosphite, di(2-ethylhexyl) (isooctylphenyl)phosphite, tri(2-cyclohexylphenyl)phosphite, tri-α-naphthyl phosphite, tri(phenylphenyl)phosphite, tri(2-phenylethyl)phosphite, ethylene phenyl phosphite, ethylene t-butyl phosphite, ethylene isohexyl phosphite, ethylene isooctyl phosphite, ethylene cyclohexyl phosphite, 2-phenoxy-1,3,2-dioxaphosphorinane, 2-butoxy-1,3,2-dioxyphosphorinane, 2-octoxy-5,5-dimethyl-dioxaphosphorinane, and 2-cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane (diphenyl-pentaerythritoldiphosphite), 3,9-di(decyloxy)-2,4,8,10-tetraoxa-3,9-diphosphaspiro (5,5)-undecane, 3,9-di(isodecyloxy)-2,4,8,10-tetraoxa-3,9-diphosphaspiro-(5,5)-undecane, 3,9-di(octadecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di(methoxy)-2,4,8,10-tetraoxa-3,9-diphosphaspiro-(5,5)-undecane, 3,9-di(-lauryloxy)-2,4,8,10-tetraoxa-3,9-diphosphaspiro-(5,5)-undecane, 3,9-di-p-tolyloxy-2,4,8,10-tetraoxa-3,9-diphosphaspiro-(5,5)-undecane; 3,9-di(methoxyethyloxy)-2,4,8,10-tetraoxa-3,9-diphosphaspiro-(5,5)-undecane; 3-methoxyethyloxy-9-isodecyloxy-2,4,8,10-tetraoxa-3,9-diphosphaspiro-(5,5)-undecane; 3,9-di(ethoxyethyloxy)-2,4,8,10-tetraoxa-3,9-diphosphaspiro-(5,5)-undecane; 3,9-di(butoxyethyloxy)-2,4,8,10-tetraoxa-3,9-diphosphaspiro-(5,5)-undecane; 3-methoxyethyloxy-9-butoxyethyloxy-2,4,8,10-tetraoxa-3,9-diphosphaspiro-(5,5)-undecane; 3,9-di(methoxyethoxyethyloxy)-2,4,8,10-tetraoxa-3,9-diphosphaspiro-(5,5)-undecane; 3,9-di(butoxyethoxyethyloxy)-2,4,8,10-tetraoxa-3,9-diphosphaspiro-(5,5)-undecane; 3,9-di(methoxyethoxyethoxyethyloxy)-2,4,8,10-tetraoxa-3,9-diphosphaspiro-(5,5)-undecane; 3,9-di(methoxy(polyethoxy)ethyloxy)-2,4,8,10-tetraoxa-3,9-diphosphaspiro-(5,5)-undecane (where the (polyethoxy) ethyloxy group has an average molecular weight of 350)3,9-di(methoxy(polyethoxy)ethyloxy)-2,4,8,10-tetraoxa-3,9-diphosphaspiro-(5,5)-undecane (where the (polyethoxy)ethyloxy group has an average molecular weight of 550).

Exemplary of the bis aryl triphosphites are: bis(4,4'-thio-bis(2-tertiary butyl-5-methyl-phenol))isooctyl phosphite, mono(4,4'-thio-bis(2-tertiary-butyl-5-methyl-phenol))di-phenyl phosphite, tri-(4,4'-n-butylidene-bis(2-tertiary-butyl-5-methyl-phenol))phosphite, (4,4'-benzylidene-bis(2-tertiary-butyl-5-methyl-phenol)-)diphenyl phosphite, isooctyl 2,2'-bis(-parahydroxyphenyl)propane phosphite, decyl 4,4'-n-butylidene-bis(2-tertiary-butyl-5-methylphenol)phosphite, tri-4,4'-thiobis(2-tertiary-butyl-5-methylphenol)phosphite, 2-ethylhexyl-2,2'-methylene-bis(4-methyl-6,1'-methylcyclohexyl)phenol phosphite, tri(2,2'-bis-(para-hydroxyphenyl)propane)phosphite, tri(4,4'-thio-bis(2-tertiary-butyl-5-methyl-phenol)phosphite, isooctyl-(2,6,-bis(2'-hydroxy-3,5-dinonylbenzyl)-4-nonyl phenyl))phosphite, tetra-tridecyl 4,4'-n-butylidene-bis(2-tertiary butyl-5-methyl phenyl)diphosphite, tetra-isooctyl 4,4'-thiobis (2-tertiary butyl-5-methyl phenyl)diphosphite, 2,2'-methylene-bis(4-methyl 6,1'-methyl cyclohexyl phenyl)polyphosphite, isooctyl-4,4'-isopropylidene-bisphenyl-polyphosphite, 2-ethylhexyl-2,2'-methylene-bis(4-methyl-6,1'-methyl-cyclohexyl)phenyl triphosphite, tetra-tridecyl-4,4'-oxydiphenyl diphosphite, tetra-n-dodecyl-4,4'-n-butylidene bis(2-tertiary-butyl-5-methylphenyl)diphosphite, tetra-tridecyl-4,4'-iso-propylidene bisphenyl diphosphite, hexa-tridecyl butane-1,1,3-tris (2'-methyl-5'-tertiary-butylphenyl-4'-)triphosphite.

Exemplary acid phosphites are di(phenyl)phosphite, monophenyl phosphite, mono-(diphenyl)phosphite, dicresyl phosphite, di-(o-isooctylphenyl)phosphite, di(p-ethylhexylphenyl)phosphite, di(p-t-octylphenyl)-phosphite, di(dimethylphenyl)phosphite, di-n-butyl phosphite, di-2-ethylhexyl phosphite, mono-2-ethylhexyl phosphite, diisooctyl phosphite, monoisooctyl phosphite, monododecyl phosphite, 2-ethylhexyl phenyl phosphite, 2-ethylhexyl-(n-octylphenyl)phosphite, monocyclohexyl phosphite, dicyclohexyl phosphite, di(2-cyclohexyl phenyl)phosphite, di-α-naphthyl phosphite, diphenyl phenyl phosphite, di(diphenyl)phosphite, di-(2-phenyl ethyl)phosphite, dibenzyl phosphite, monobenzyl phosphite, n-butyl cresyl phosphite and didodecyl phosphite, cresyl phosphite, t-octylphenyl phosphite, ethylene phosphite, butyl cresyl phosphite, isooctyl monotolyl phosphite and phenyl cyclohexyl phosphite.

Exemplary of the bis aryl acid phosphites are: bis(4,4'-thio-bis(2-tertiary-butyl-5-methyl-phenol))-phosphite, (4,4'-thio-bis(2-tertiary-butyl-5-methyl-phenol))phenyl phosphite, bis(4,4'-n-butylidene-bis(2-tertiary-butyl-5-methyl-phenol))phosphite, mono-(4,4'-benzylidene-bis(2-tertiary-butyl-5-methyl-phenol))-phosphite, mono(2,2'-bis-(parahydroxyphenyl)-propane)phosphite, mono(4,4'-n-butylidene-bis(-2-tertiary-butyl-5-methyl-phenol)phosphite, bis(4,4'-thiobis(2-tertiary-butyl-5-methylphenol))phosphite, mono-2-ethylhexyl-mono-2,2'-methylene-bis(4-methyl-6,1'-methylcyclohexyl)phenol phosphite, bis(2,2'-bis-(parahydroxyphenyl)propane)phosphite, monoisooctyl mono(4,4'thio-bis(2-tertiary-butyl-5-methyl-phenol))-phosphite, isooctyl-(2,6-bis(2'-hydroxy-3,5-dinonylbenzyl)-4-nonyl phenyl))phosphite, tri-tridecyl 4,4'-n-butylidene-bis(2-tertiary-butyl-5-methyl phenyl)diphosphite, triisooctyl 4,4'-thiobis(2-tertiary-butyl-5-methyl phenyl)diphosphite, bis(2,2'-methylene-bis(4-methyl-6,1'-methyl cyclohexyl phenyl))phosphite, isooctyl-4,4'-isopropylidene-bis-phenyl phosphite, monophenyl mono(2,2'-methylene-bis(4-methyl-6,1'-methyl-cyclohexyl))triphosphite, di-tridecyl-4,4'-oxydiphenyl diphosphite, di-n-dodecyl-4,4'-n-butylidene bis(2-tertiary-butyl-5-methylphenyl)diphosphite, di-tridecyl-4,4'-isopropylene bisphenyl diphosphite, tetra-tridecyl butane-1,1,3-tris(2'-methyl-5'-tertiary-butylphenyl-4-)triphosphite.

The stabilizer system can also include an alkaline earth metal carboxylate. The alkaline earth metal salts of an aliphatic monocarboxylic acid having from about eight to about twenty-four carbon atoms are exemplary. Such metal salts are widely used in the processing of polyvinyl chloride resins, particularly by extrusion, because of their lubricating characteristics. Exemplary alkaline earth metals are calcium, strontium and barium, and exemplary organic acids are lauric acid, 2-ethyl hexoic acid, undecylenic acid, capric acid, caproic acid, myristic acid, palmitic acid, stearic acid, oleic acid, linoleic acid, ricinoleic acid, linolenic acid, behenic acid and eicosanoic acid.

These acid salts are particularly advantageously prepared from the mixed fatty acids obtained by saponification of natural fats and waxes, such as coconut oil fatty acids, tallow fatty acids, montan wax fatty acids, castor oil fatty acids, corn oil fatty acids, fish oil fatty acids, sesame seed oil fatty acids, soya oil fatty acids, and tung oil fatty acids. Also useful are the partially saponified ester waxes, such as esters of montan wax partially saponified with lime, and the synthetic aliphatic monocarboxylic acids.

Exemplary alkaline earth metal carboxylates that can be employed include calcium stearate, barium stearate, strontium stearate, calcium 2-ethylhexanoate, calcium oleate, barium oleate, calcium laurate, barium laurate, strontium caprylate, calcium palmitate, calcium caproate, and calcium eicosanoate, barium neodecanoate, barium octoate, strontium octoate, calcium decanoate and calcium undecanoate.

Mixtures of alkaline earth metal carboxylates can also be used, such as mixtures of barium and calcium stearate, barium and calcium octoate, barium and calcium oleate, barium and calcium myristate, and barium and calcium palmitate, as well as the calcium salts of coconut fatty acids, barium salts of coconut fatty acids, and strontium salts of tallow fatty acids.

Any of the metal carboxylates disclosed in U.S. Pat. Nos. 3,887,508 and 4,029,618 to Dieckmann can also be used.

Epoxidized triglyceride esters that can be used together with the antimony mercaptocarboxylic acid ester and any other stabilizers, and homogeneously blended therewith, include any epoxidized previously ethylenically unsaturated fatty oils and fatty acid esters. Such oils and esters may have had one or more ethylenically unsaturated groups per molecule. Fatty oils, as is well known, are usually composed of varying proportions of glycerides of organic fatty acids including both saturated and unsaturated fatty acids, of which only the unsaturated groups have been epoxidized, the fatty acids having from about eight to about twenty-four carbon atoms.

Exemplary are epoxidized soyabean oil, epoxidized cottonseed oil, epoxidized beef tallow, epoxidized sheep tallow, epoxidized fish oils of various types, such as epoxidized menhaden oil, epoxidized cod liver oil, epoxidized shark oil, epoxidized sperm oil, epoxidized whale oil, exoxidized herring oil, epoxidized peanut oil, epoxidized linseed oil, epoxidized sunflower seed oil, epoxidized safflower seed oil, epoxidized coconut oil epoxidized palm oil, epoxidized lard oil, epoxidized perilla oil, epoxidized palm kernel oil, epoxidized poppyseed oil, epoxidized rapeseed oil, epoxidized sesame seed oil, epoxidized hempseed oil, epoxidized cocoa oil, epoxidized acorn oil, epoxidized apricot kernel oil, epoxidized beechnut oil, epoxidized cherry kernel oil, and epoxidized corn oil, as well as epoxidized triglyceride esters mixed with epoxidized esters of the unsaturated fatty acids and monohydric and other polyhydric alcohols including epoxidized esters of oleic acid, linoleic acid, linolenic acid, ricinoleic acid, crotonic acid, and isocrotonic acid, with ethylene glycol, ethyl alcohol, pentaerythritol, butyl alcohol, mannitol, sorbitol, lauryl alcohol and stearyl alcoho.

The stabilizer system in accordance with the invention, containing the antimony mercaptocarboxylic acid ester or mixed acid ester, and any mercaptocarboxylic acid ester and/or ortho-dihydric phenol, can be prepared by simple blending of the ortho-dihydric phenol and antimony mercaptocarboxylic acid ester and mercaptocarboxylic acid ester.

If desired, the ortho-dihydric phenol can be added to the reaction mixture in the course of preparation of the antimony mercaptocarboxylic acid ester. When ortho-dihydric phenol is present, the final reaction product contains the ortho-dihydric phenol reacted with the antimony mercaptocarboxylic acid ester.

It is also possible to react antimony trioxide with the ortho-dihydric phenol in preparing an antimony phenolate of the type:

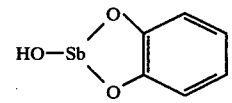

The antimony phenolate is then dissolved in either mercaptocarboxylic acid ester, prior to reaction thereof with antimony trioxide or antimony trichloride and alkali, to form the antimony mercaptocarboxylic acid ester, or the antimony phenolate can be dissolved directly in the antimony mercaptocarboxylic acid ester, to prepare the stabilizer system.

The proportion of antimony mercaptocarboxylic acid ester and mercaptocarboxylic acid ester is within the range from about 90 to about 25 parts antimony mercaptocarboxylic acid ester to from about 10 to about 75 parts of mercaptocarboxylic acid ester, and preferably within the range from about 40 to about 60 parts antimony mercaptocarboxylic acid ester to from about 60 to about 40 parts mercaptocarboxylic acid ester. The amount of mercaptocarboxylic acid ester can be selected within the stated range to give an enhanced synergistic effect in imparting resistance to early discoloration, as compared to either antimony mercaptocarboxylic acid or ester, or mercaptocarboxylic acid ester, alone.

The proportion of the blend of antimony mercaptocarboxylic acid or ester or mixed acid ester and mercaptocarboxylic acid ester to ortho-dihydric phenol in the stabilizer systems of the invention can be within the range from about 100:1 to about 2:1, and preferably from about 50:1 to about 9:1.

The proportion of alkaline earth metal carboxylate to the blend of antimony mercaptocarboxylic acid or ester and mercaptocarboxylic acid ester can be within the range from about 10:1 to about 1:10, and preferably from about 3:1 to about 1:3.

The weight ratio of epoxidized triglyceride ester:-blend of antimony compound and mercaptocarboxylic acid ester can be within the range from about 10:1 to about 1:10 and preferably from about 3:1 to about 1:3.

The stablizer systems in accordance with the invention can be used as stabilizers with any polyvinyl chloride resin formulation. The term "polyvinyl chloride" as used herein is inclusive of any polymer formed at least in part of the recurring group

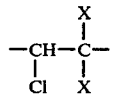

and having a chlorine content in excess of 40%. In this group, the X group can each be either hydrogen or chlorine. In polyvinyl chloride homopolymers each of the X groups is hydrogen. Thus, the term includes not only polyvinyl chloride homopolymers but also after-chlorinated polyvinyl chloride such as those disclosed in British patent No. 893,288 and also copolymers of vinyl chloride in a major proportion and other copolymerizable monomers in a minor proportion, such as copolymers of vinyl chloride and vinyl acetate, copolymers of vinyl chloride with maleic or fumaric acids or esters, and copolymers of vinyl chloride with styrene, propylene, and ethylene. The invention also is applicable to mixtures of polyvinyl chloride in a major proportion with other synthetic resins such as chlorinated polyethylene or a copolymer of acrylonitrile, butadiene and styrene. Among the polyvinyl chlorides which can be stabilized are the uniaxially-stretch oriented polyvinyl chlorides described in U.S. Pat. No. 2,984,593 to Isaksem et al, that is, syndiotactic polyvinyl chloride as well as atactic and isotactic polyvinyl chlorides.

The stabilizer systems of the invention are particularly useful with rigid polyvinyl chloride resin formulations. These are defined as containing no or only up to 10% plasticizer. The stabilizer systems are also useful with 10% and more plasticizer, up to about 50% plasticizer, in plasticized formulations. Plasticizers which can be employed in rigids, to impart an improved processability without impairing the rigidity of the formulation or in plasticized formulations, include dioctyl phthalate, dioctyl sebacate, and tricresyl phosphate. Where a plasticizer is employed, it can be used in an amount within the range from about 0.5 to about 10 parts per 100 parts by weight of the resin.

Also useful plasticizers are the epoxy higher fatty acid esters having from about twenty to about one hundred fifty carbon atoms.

Impact modifiers, for improving the toughness or impact-resistance of unplasticized resins, can also be added to the resin compositions stabilized by the present invention in minor amounts of usually not more than 10%. Examples of such impact modifiers include chlorinated polyethylene, ABS and MBS ethylene-vinyl acetate copolymers, and polyacrylate-butadiene graft copolymers.

The total amount of stabilizer system in accordance with the invention is sufficient to impart the desired resistance to the development of early discoloration at working temperatures of 375° F. and above for at least 10 minutes up to but not necessarily exceeding the first 20 to 30 minutes of heating. The more onerous the conditions to which the resin will be subjected during working, the greater will be the amount of stabilizer system required. Generally, as little as 0.1% total stabilizer by weight of the resin will improve the resistance of the development of early discoloration. There is no critical upper limit on the amount, but amounts above about 10% by weight of the resin do not give an increase in stabilizing effectiveness commensurate with the additional stabilizer employed. Preferably, the amount is within the range from about 0.20 to about 2% by weight of the resin.

If a stabilizer system with other stabilizers is used, of this amount, from about 0.007 to about 9.8% by weight, preferably from about 0.18 to 1.95% by weight, is antimony mercaptocarboxylic acid ester, together with any optional additional stabilizer such as from 0.01 to about 7.5% by weight, preferably from about 0.2 to about 1.5% by weight, is mercaptocarboxylic acid ester: from about 0.001 to about 1% by weight, perferably from about 0.01 to about 0.5% by weight, is ortho-dihydric phenol, if present; and from about 0.1 to about 1.5% by weight is alkaline earth metal carboxylate, if present, and from about 0.1 to about 1.5% by weight is epoxidized triglyceride ester, if present.

The stabilizer of the invention or stabilizer system as above are each extremely effective when used alone, but they can be employed together with other polyvinyl chloride resin stabilizers, including organotin compounds, if special effects are desired. The stabilizer of the invention or stabilizer system as above will in this event be the major stabilizer, and the additional stabilizer will supplement the stabilizing action of the former, the amount of the antimony mercaptocarboxylic acid ester or stabilizer system containing the same being within the range from about 0.1 to about 10 parts by weight per 100 parts of the resin, and the additional stabilizer being in the amount of from about 0.05 to about 5 parts per 100 parts of the resin.

Among the additional metallic stabilizers are included polyvalent metal salts of medium and of high molecular weight phenols, with metals such as calcium, tin, barium, zinc, magnesium, and strontium. The nonmetallic stabilizers include antioxidants, organic phosphites, epoxy compounds (other than the triglycerides referred to above), polyhydric alcohols, and the like. Epoxy compounds are especially useful, and typical compounds are described in U.S. Pat. No. 2,997,454.

The stabilizer and stabilizer systems of this invention can be formulated for marketing by mixing the antimony mercaptocarboxylic acid or ester or a previously prepared blend thereof with other stabilizers, desirably after heating at an elevated temperature, with an inert diluent or with any liquid or wax lubricant combination, and/or with any plasticizer in suitable concentrations ready to be added to the resin composition to give an appropriate stabilizer and lubricant or plasticizer concentration in the resin. Other stabilizers and stabilizer adjuncts can be incorporated as well.

The preparation of the polyvinyl chloride resin composition is easily accomplished by conventional procedures. The selected stabilizer combination is formed as described above, and then is blended with the polyvinyl chloride resin, or alternatively, the components are blended individually in the resin, using, for instance, a two or three roll mill, at a temperature at which the mix is fluid and thorough blending facilitated, milling the resin composition including any plasticizer at from 250° to 375° F. for a time sufficient to form a homogeneous mass, five minutes, usually. After the mass is uniform, it is extruded in the usual way.

For the commercial processing of rigid polyvinyl chloride, the stabilizer is conveniently mixed with all or a portion of the polymer to be stabilized with vigorous agitation under such conditions of time and temperature that the stabilizer is sufficiently imbibed by the polymer to produce a dry, free-flowing powder. The well-known Henschel mixer is well suited to this procedure.

EXAMPLES I to V

An unpigmented rigid, i.e., nonplasticized, polyvinyl chloride resin formulation was prepared having the following composition:

| Component | Parts by Weight Example I |
|---|---|
| Polyvinyl chloride resin polymer (Diamond 40) | 100 |
| Calcium stearate | 0.6 |
| Wax 160 (160° F. m.p. paraffin) | 0.1 |
| Low molecular weight polyethylene | 0.1 |
| Stabilizers (as shown in Table I) | (as in Table I) |

The stabilizer was mixed in the resin in the proportion indicated in Table I below on a two-roll mill to form a homogeneous sheet and sheeted off. Strips were cut from the sheet and heated in an oven at 175° C. for up to ninety minutes. Pieces of each strip were removed at fifteen minute intervals, and affixed to cards, to show the progressive development of the discoloration. During the first fifteen to thirty minutes of heating early discoloration manifests itself. After thirty minutes of heating, long term heat stability can be observed.

Color of each sample was rated in accordance with color scale "A" as follows:

| Scale A |
|---|
| 0 - Clear and colorless |
| 1 - Trace of color |
| 2 - Very light tan |
| 3 - Light tan |
| 4 - Very light amber |
| 5 - Light amber |
| 6 - Medium dark yellow |
| 7 - Dark amber |
| 8 - Green-brown |
| 9 - Green-black |

The stabilizers used in each resin composition and the results obtained are shown in Table I:

TABLE I

| Example No. | Stabilizer | % Sb | Parts per 100 parts resin | Initial unexposed color | After (minutes) 15 | 30 | 45 | 60 | 75 | 90 |
|---|---|---|---|---|---|---|---|---|---|---|
| Control 1 | Antimony tris (iso-octyl thioglycolate) | 16.7 | 0.4 | 0 | 1 | 2 | 3 | 4 | 5 | 7 |
| Example I | Product of Example 9 | 14.5 | 0.4 | 0 | 1 | 1 | 2 | 2 | 3 | 3 |
| Example II | Product of Example 2 | 11.8 | 0.4 | 0 | 1 | 1 | 1 | 2 | 2 | 2 |
| Example III | Product of Example 2 | 11.8 | 0.3 | 0 | 1 | 1 | 2 | 2 | 3 | 3 |
| Control 2 | Antimony tris (iso-octyl thioglycolate) t-butyl catechol | 16.7 | 0.4 0.02 | 0 | 1 | 1 | 2 | 3 | 4 | 6 |
| Example IV | Product of Example 2 t-butyl-catechol | 11.8 | 0.3 0.02 | 0 | 1 | 1 | 1 | 2 | 2 | 5 |
| Example V | Product of Example 9 t-butyl-catechol | 14.5 | 0.4 0.02 | 0 | 1 | 1 | 1 | 2 | 2 | 5 |

Despite a lower antimony content by weight, each of the stabilizers according to this invention imparts unexpectedly better early color and long term stability than the Control antimony stabilizer, with or without added t-butyl-catechol.

EXAMPLES VI TO IX

Rigid, i.e., nonplasticized, polyvinyl chloride resin formulations were prepared having the following composition:

| Component | Parts by Weight |
|---|---|
| Polyvinyl chloride resin homopolymer (Diamond 40) | 100 |
| Titanium dioxide (pigment) | 1 |
| Calcium carbonate | 0.6 |
| Calcium stearate | 1 |
| Acrylic processing aid | 1 |
| Wax 160 (160° F. m.p. paraffin) | 1 |
| Low molecular weight polyethylene | 0.2 |
| Stabilizer (as shown in Table II) | 0.4 |

The stabilizer was mixed in the resin in the proportion indicated in Table II below on a two-roll mill to form a homogeneous sheet, and sheeted off. Strips were cut from the sheet and heated in an oven at 175° C. to determine the onset of early discoloration during the first stages of heating. Pieces of each strip were removed at fifteen minute intervals, and affixed to cards, to show the progressive development of the discoloration for the first fifteen to thirty minutes. The effect on long term heat stability was determined by continuing the test for 120 minutes.

The development of early discoloration is evaluated by the intensity of tint formed. The observed discoloration of each sample is described in Table II. The following abbreviations are used:

w=white
ow=off white
c=cream
t=tan
b=brown
cc, tt and bb indicate darker shades of cream, tan and brown, respectively.

TABLE II

| Example No | Stabilizer | % Sb | Initial unexposed color | After (minutes) | | | | | | | |
|---|---|---|---|---|---|---|---|---|---|---|---|
| | | | | 15 | 30 | 45 | 60 | 75 | 90 | 105 | 120 |
| Control 3 | Antimony tris (isooctyl thioglycolate) | 16.7 | w | ow | ow | t | tt | tt | b | b | b |
| Example VI | Product of Example 2 | 11.8 | w | w | w | c | cc | t | t | tt | tt |
| Example VII | Product of Example 3 | 12.64 | w | w | w | c | cc | t | t | tt | tt |
| Example VIII | Product of Example 4 | 7.59 | w | w | w | c | cc | t | t | tt | tt |
| Example IX | Product of Example 5 | 10.90 | w | w | ow | c | cc | t | t | tt | tt |

The results show that each of the antimony stabilizer products of this invention imparts better heat stability, both in preventing early discoloration and in lessening the severity of discoloration in the long term, than antimony tris (isooctyl thioglycolate).

EXAMPLES X TO XIII

Rigid, i.e., nonplasticized, polyvinyl chloride resin formulations were prepared having the following composition:

| Component | Parts by Weight |
|---|---|
| Polyvinyl chloride resin homopolymer (Diamond 40) | 100 |
| Titanium dioxide (pigment) | 1 |
| Calcium carbonate | 0.6 |
| Calcium stearate | 1 |
| Acrylic processing aid | 1 |
| Wax 160 (160° F.m.p. paraffin) | 1 |
| Low molecular weight polyethylene | 0.2 |
| Catechol | 0.02 |
| Stabilizer (as in Table III) | 0.4 |

The stabilizer was mixed in the resin in the proportion indicated in Table III below on a two-roll mill to form a homogeneous sheet, and sheeted off. Strips were cut from the sheet and heated in an oven at 175° C. to determine the onset of early discoloration during the first stages of heating. Pieces of each strip were removed at fifteen minute intervals, and affixed to cards, to show the progressive development of the discoloration for the first fifteen to thirty minutes. The effect on long term heat stability was determined by continuing the test for 120 minutes.

The development of early discoloration is evaluated by the intensity of tint formed. The observed discoloration of each sample is described in Table III. The following abbreviations are used:

w=white
ow=off white
c=cream
t=tan
b=brown
cc, tt, and bb indicate darker shades of cream, tan and brown, respectively.

TABLE III

| Example No. | Stabilizer | % Sb | Initial unexposed color | After (minutes) | | | | | | | |
|---|---|---|---|---|---|---|---|---|---|---|---|
| | | | | 15 | 30 | 45 | 60 | 75 | 90 | 105 | 120 |
| Control A | Antimony tris(isooctyl thioglycolate) | 16.7 | w | w | w | C | t | tt | b | bb | bb |
| Example X | Product of Example 2 | 11.8 | w | w | w | ow | c | cc | cc | t | t |
| Example XI | Product of Example 3 | 12.64 | w | w | w | ow | c | cc | cc | t | t |
| Example XII | Product of Example 4 | 7.59 | w | w | w | ow | c | cc | t | t | |
| Example XIII | Product of Example 5 | 10.90 | w | w | w | c | cc | cc | t | t | t |

The results show that each of the antimony stabilizer products of this invention imparts better heat stability, both in preventing early discoloration and in lessening the severity of discoloration in the long term, than antimony tris (isooctyl thioglycolate). The response to catechol addition also differs. With antimony tris (isooctyl thioglycolate) the improved resistance to early discoloration resulting from catechol addition is compromised by more severe discoloration later, while with the products of this invention catechol addition is helpful both to early color control and to long term heat stability.

Having regard to the foregoing disclosure, the following is claimed as inventive and patentable embodiments thereof:

1. Antimony mercaptocarboxylic acid esters having the formula:

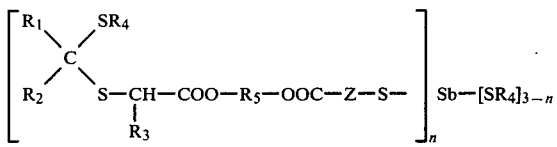

wherein:
R$_1$ is selected from the group consisting of hydrogen, alkyl having from one to about eighteen carbon atoms and alkylene linked with R$_2$ in a ring having from three to about eight carbon atoms;
R$_2$ is selected from the group consisting of alkyl having from one to about eighteen carbon atoms, phenyl, and alkylene linked with R$_1$ in a ring having from three to about eight carbon atoms;
R$_3$ is selected from the group consisting of hydrogen and alkyl having from one to three carbon atoms;
R$_4$ is selected from the group consisting of alkyl, aryl, alkylaryl, alkoxycarbonyl-alkylene and acyloxyalkylene having from three to about twenty carbon atoms, the alkylene having from two to about six carbon atoms;
R$_5$ is selected from the group consisting of alkylene and cycloalkylene having from one to about eighteen carbon atoms, and such groups having from one to four hydroxyl groups;
Z is a bivalent alkylene group having from one to five carbon atoms and carrying the sulfur in a position alpha or beta to —OOC—; and
n is a number from 1 to 3.

2. Antimony mercaptocarboxylic acid esters according to claim 1 in which R$_1$ is hydrogen or alkyl; and R$_2$ is alkyl.

3. Antimony mercaptocarboxylic acid esters according to claim 1 in which R$_1$ is hydrogen or alkyl; and R$_2$ is phenyl.

4. Antimony mercaptocarboxylic acid esters according to claim 1 in which R$_1$ and R$_2$ are alkylene linked in a ring having from three to about eight carbon atoms.

5. Antimony mercaptocarboxylic acid esters according to claim 1 in which R$_3$ is hydrogen.

6. Antimony mercaptocarboxylic acid esters according to claim 1 in which R$_3$ is alkyl.

7. Antimony mercaptocarboxylic acid esters according to claim 1 in which R$_4$ is aryl or alkyl.

8. Antimony mercaptocarboxylic acid esters according to claim 1 in which R$_4$ is alkylaryl.

9. Antimony mercaptocarboxylic acid esters according to claim 1 in which R$_4$ is alkoxycarbonyl-alkylene.

10. Antimony mercaptocarboxylic acid esters according to claim 1 in which R$_4$ is acyloxyalkylene.

11. Antimony mercaptocarboxylic acid esters according to claim 1 in which R$_5$ is alkylene.

12. Antimony mercaptocarboxylic acid esters according to claim 1 in which R$_5$ is cycloalkylene.

13. Antimony mercaptocarboxylic acid esters according to claim 1 in which Z is methylene.

14. Antimony mercaptocarboxylic acid esters according to claim 1 in which Z is ethylene.

15. Antimony mercaptocarboxylic acid esters according to claim 1 in which Z is propylene.

16. Antimony mercaptocarboxylic acid esters according to claim 1 in which n is 1.

17. Antimony mercaptocarboxylic acid esters according to claim 1 in which n is 2.

18. Antimony mercaptocarboxylic acid esters according to claim 1 in which n is 3.

19. Antimony mercaptocarboxylic acid esters according to claim 1 in which R$_1$ is hydrogen or alkyl; R$_2$ is alkyl; R$_3$ is hydrogen; R$_4$ is alkoxycarbonyl-alkylene; and R$_5$ is alkylene.

20. Antimony mercaptocarboxylic acid esters according to claim 1 in which R$_1$ is hydrogen or alkyl; R$_2$ is alkyl; R$_3$ is hydrogen; R$_4$ is acyloxyalkylene; and R$_5$ is alkylene.

21. Antimony mercaptocarboxylic acid esters according to claim 1 in which R$_1$ and R$_2$ are alkylene linked in a ring having from three to about eight carbon atoms; R$_3$ is hydrogen; R$_4$ is alkoxycarbonyl-alkylene; and R$_5$ is alkylene.

22. Antimony mercaptocarboxylic acid esters according to claim 1 in which R$_1$ and R$_2$ are alkylene linked in a ring having from three to about eight carbon atoms; R$_3$ is hydrogen; R$_4$ is acyloxyalkylene; and R$_5$ is alkylene.

23. Mercaptocarboxylic acids having the formula:

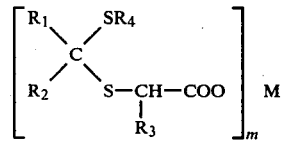

wherein:
R$_1$ is selected from the group consisting of hydrogen, alkyl having from one to about eighteen carbon atoms and alkylene linked with R$_2$ in a ring having from three to about eight carbon atoms;
R$_2$ is selected from the group consisting of alkyl having from one to about eighteen carbon atoms, phenyl, and alkylene linked with R$_1$ in a ring having from three to about eight carbon atoms;
R$_3$ is selected from the group consisting of hydrogen and alkyl having from one to three carbon atoms;
R$_4$ is selected from the group consisting of alkyl, aryl, alkylaryl, alkoxycarbonyl-alkylene and acyloxyalkylene having from three to about twenty carbon atoms, the alkylene having from two to about six carbon atoms;
M is a monovalent or polyvalent metal cation; and
m is a number from 1 to not exceeding the valence of M, any remaining bonds of the valence not taken up by the mercaptocarboxylic acid group being taken up by hydrogen H.

24. Mercaptocarboxylic acids according to claim 23 in which R$_1$ is hydrogen or alkyl; R$_2$ is alkyl; R$_3$ is hydrogen; and R$_4$ is alkoxycarbonyl-alkylene.

25. Mercaptocarboxylic acids according to claim 23 in which $R_1$ is hydrogen or alkyl; $R_2$ is alkyl; $R_3$ is hydrogen; and $R_4$ is acyloxyalkylene.

26. Mercaptocarboxylic acids according to claim 23 in which $R_1$ is hydrogen or alkyl; $R_2$ is alkyl; $R_3$ is hydrogen; and $R_4$ is aryl or alkyl.

27. Mercaptocarboxylic acids according to claim 23 in which $R_1$ is hydrogen or alkyl; $R_2$ is alkyl; $R_3$ is hydrogen; and $R_4$ is alkylaryl.

28. Mercaptocarboxylic acids according to claim 25 in which $R_1$ and $R_2$ are alkylene linked in a ring; $R_3$ is hydrogen; and $R_4$ is alkoxycarbonyl-alkylene.

29. Mercaptocarboxylic acids according to claim 25 in which $R_1$ and $R_2$ are alkylene linked in a ring; $R_3$ is hydrogen; and $R_4$ is acyloxalkylene.

30. Polyol mercaptocarboxylic acid monoesters having the formula:

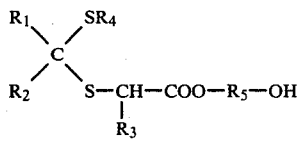

wherein:
- $R_1$ is selected from the group consisting of hydrogen, alkyl having from one to about eighteen carbon atoms and alkylene linked with $R_2$ in a ring having from three to about eight carbon atoms;
- $R_2$ is selected from the group consisting of alkyl having from one to about eighteen carbon atoms, phenyl, and alkylene linked with $R_1$ in a ring having from three to about eight carbon atoms;
- $R_3$ is selected from the group consisting of hydrogen and alkyl having from one to three carbon atoms;
- $R_4$ is selected from the group consisting of alkyl, aryl, alkylaryl, alkoxycarbonyl-alkylene and acyloxyalkylene having from three to about twenty carbon atoms, the alkylene having from two to about six carbon atoms; and
- $R_5$ is selected from the group consisting of alkylene and cycloalkylene having from one to about eighteen carbon atoms, and such groups having from one to four hydroxyl groups.

31. Polyol mercaptocarboxylic acid monoesters according to claim 30 in which $R_1$ is hydrogen or alkyl; $R_2$ is alkyl; $R_3$ is hydrogen; $R_4$ is alkoxycarbonyl-alkylene; and $R_5$ is alkylene.

32. Polyol mercaptocarboxylic acid monoesters according to claim 30 in which $R_1$ is hydrogen or alkyl; $R_2$ is alkyl; $R_3$ is hydrogen; $R_4$ is acyloxyalkylene; and $R_5$ is alkylene.

33. Polyol mercaptocarboxylic acid monoesters according to claim 30 in which $R_1$ and $R_2$ are alkylene linked in a ring; $R_3$ is hydrogen; $R_4$ is alkoxycarbonyl-alkylene; and $R_5$ is alkylene.

34. Polyol mercaptocarboxylic acid monoesters according to claim 30 in which $R_1$ and $R_2$ are alkylene linked in a ring; $R_3$ is hydrogen; $R_4$ is acyloxyalkylene; and $R_5$ is alkylene.

35. Bis-mercaptocarboxylic acid polyesters having the formula:

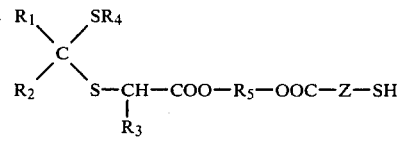

wherein:
- $R_1$ is selected from the group consisting of hydrogen, alkyl having from one to about eighteen carbon atoms and alkylene linked with $R_2$ in a ring having from three to about eight carbon atoms;
- $R_2$ is selected from the group consisting of alkyl having from one to about eighteen carbon atoms, phenyl, and alkylene linked with $R_1$ in a ring having from three to about eight carbon atoms;
- $R_3$ is selected from the group consisting of hydrogen and alkyl having from one to three carbon atoms;
- $R_4$ is selected from the group consisting of alkyl, aryl, alkylaryl, alkoxycarbonyl-alkylene and acyloxyalkylene having from three to about twenty carbon atoms, the alkylene having from two to about six carbon atoms;
- $R_5$ is selected from the group consisting of alkylene and cycloalkylene having from one to about eighteen carbon atoms, and such groups having from one to four hydroxyl groups; and
- Z is a bivalent alkylene group having from one to five carbon atoms and carrying the sulfur in a position alpha or beta to —OOC—.

36. Bis-mercaptocarboxylic acid polyesters according to claim 35 in which $R_1$ is hydrogen or alkyl; $R_2$ is alkyl; $R_3$ is hydrogen; $R_4$ is alkoxycarbonyl-alkylene; and $R_5$ is alkylene.

37. Bis-mercaptocarboxylic acid polyesters according to claim 35 in which $R_1$ is hydrogen or alkyl; $R_2$ is alkyl; $R_3$ is hydrogen; $R_4$ is acyloxyalkylene; and $R_5$ is alkylene.

38. Bis-mercaptocarboxylic acid polyesters according to claim 35 in which $R_1$ and $R_2$ are alkylene linked in a ring; $R_3$ is hydrogen; $R_4$ is alkyoxycarbonyl-alkylene; and $R_5$ is alkylene.

39. Bis-mercaptocarboxylic acid polyesters according to claim 35 in which $R_1$ and $R_2$ are alkylene linked in a ring; $R_3$ is hydrogen; $R_4$ is acyloxyalkylene; and $R_5$ is alkylene.

40. A stabilizer composition for polyvinyl chloride resins comprising an antimony compound of claim 1 and another polyvinyl chloride resin stabilizer.

41. A stabilizer composition for polyvinyl chloride resins comprising a mercaptocarboxylic acid of claim 23 and another polyvinyl chloride resin stabilizer.

42. A stabilizer composition for polyvinyl chloride resins comprising a polyol mercaptocarboxylic acid monoester of claim 30 and another polyvinyl chloride resin stabilizer.

43. A stabilizer composition for polyvinyl chloride resins comprising a bis-mercaptocarboxylic acid polyester of claim 35 and another polyvinyl chloride resin stabilizer.

44. Polyvalent metal mercaptocarboxylic acid ester salts having the formula:

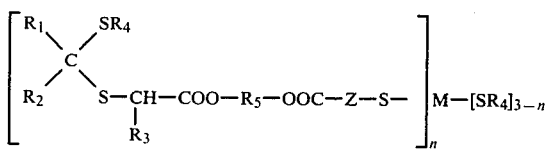

wherein:
- $R_1$ is selected from the group consisting of hydrogen, alkyl having from one to about eighteen carbon atoms and alkylene linked with $R_2$ is a ring having from three to about eight carbon atoms;
- $R_2$ is selected from the group consisting of alkyl having from one to about eighteen carbon atoms, phenyl, and alkylene linked with $R_1$ in a ring having from three to about eight carbon atoms;
- $R_3$ is selected from the group consisting of hydrogen and alkyl having from one to three carbon atoms;
- $R_4$ is selected from the group consisting of alkyl, aryl, alkylaryl, alkoxycarbonyl-alkylene and acyloxyalkylene having from three to about twenty carbon atoms, the alkylene having from two to about six carbon atoms;
- $R_5$ is selected from the group consisting of alkylene and cycloalkylene having from one to about eighteen carbon atoms, and such groups having from one to four hydroxyl groups;
- Z is a bivalent alkylene group having from one to five carbon atoms and carrying the sulfur in a position alpha or beta to —OOC—;
- M is a polyvalent metal cation; and
- n is a number from 1 to the maximum valence of the polyvalent metal cation.

45. Polyvalent metal mercaptocarboxylic acid ester salts according to claim 44 in which the polyvalent metal is selected from the group consisting of antimony, tin, calcium and zinc.

46. A process for preparing a polyvalent metal mercaptocarboxylic acid ester salt having the formula:

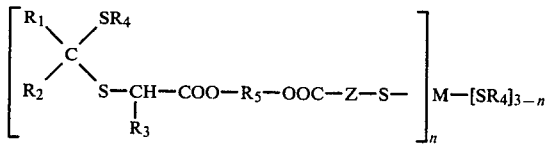

wherein:
- $R_1$ is selected from the group consisting of hydrogen, alkyl having from one to about eighteen carbon atoms and alkylene linked with $R_2$ in a ring having from three to about eight carbon atoms;
- $R_2$ is selected from the group consisting of alkyl having from one to about eighteen carbon atoms, phenyl, and alkylene linked with $R_1$ in a ring having from three to about eight carbon atoms;
- $R_3$ is selected from the group consisting of hydrogen and alkyl having from one to three carbon atoms;
- $R_4$ is selected from the group consisting of alkyl, aryl, alkylaryl, alkoxycarbonyl-alkylene and acyloxyalkylene having from three to about twenty carbon atoms, the alkylene having from two to about six carbon atoms;
- $R_5$ is selected from the group consisting of alkylene and cycloalkylene having from one to about eighteen carbon atoms, and such groups having from one to four hydroxyl groups;
- Z is a bivalent alkylene group having from one to five carbon atoms and carrying the sulfur in a position alpha or beta to —OOC—;
- M is a polyvalent metal cation; and
- n is a number from 1 to the maximum valence of the polyvalent metal cation; comprising the following steps:

(1) reacting an aldehyde or ketone $R_1R_2C{=}O$ with an α-mercaptocarboxylic acid,

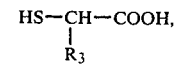

resulting in addition of the mercapto group of the α-mercaptocarboxylic acid to the keto group of the aldehyde or ketone;

(2) reacting the resulting substituted cyclic thiolactone with a mercaptide and an acid catalyst having a pK value of at most about 4, resulting in rupture of the lactone ring, and the formation of the corresponding mercaptocarboxylic acid, with the organic radical of the mercaptide becoming attached to the keto carbon atom of the starting aldehyde or ketone;

(3) esterifying the mercaptocarboyxlic acid with a polyol $HOR_5OH$, obtaining the polyol monoester;

(4) esterifying the free alcohol group of the polyol monoester with a mercaptocarboxylic acid HS—Z—COOH to form the corresponding ester with a free mercapto group; and (5) reacting the free mercapto group of this ester with a polyvalent metal compound to form the corresponding polyvalent metal mercaptocarboxylic acid ester salt.

47. A process according to claim 46 in which the mercaptide in Step (2) is selected from the group consisting of aryl mercaptans, β- and β-mercaptocarboxylic acid esters, and mercaptoalcohol esters.

48. A process according to claim 46 in which Step (1) is carried out under azeotroping water-removing conditions under reflux in an inert solvent; and then there is added a stoichiometric amount of mercaptide; and the Step (2) reaction is carried out under a reflux at a temperature within the range from about 100 to about 180° C. until the corresponding mercaptocarboxylic acid is formed.

49. A process according to claim 48 in which to the Step (2) reaction mixture is added a stoichiometric amount of polyol, and the mercaptocarboxylic acid is esterified by heating under reflux under azeotroping water-removing conditions until the corresponding polyol monoester is obtained.

50. A process according to claim 46, which comprises preparing the antimony salt from the mercaptocarboxylic acid polyol monoester of Step (4) by heating the mercaptoester with antimony trioxide, and removing the reaction water.

51. A process for preparing mercaptocarboxylic acid esters having the formula:

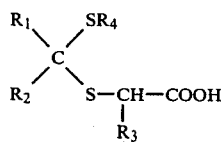

wherein:
R₁ is selected from the group consisting of hydrogen, alkyl having from one to about eighteen carbon atoms and alkylene linked with R₂ in a ring having from three to about eight carbon atoms;
R₂ is selected from the group consisting of alkyl having from one to about eighteen carbon atoms, phenyl, and alkylene linked with R₁ in a ring having from three to about eight carbon atoms;
R₃ is selected from the group consisting of hydrogen and alkyl having from one to three carbon atoms; and
R₄ is selected from the group consisting of alkyl, aryl, alkylaryl, alkoxycarbonyl-alkylene and acyloxyalkylene having from three to about twenty carbon atoms, the alkylene having from two to about six carbon atoms;
which comprises reacting stoichiometric amounts of a mercaptide with an oxathiolanone having the formula:

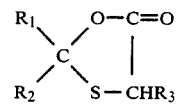

in the presence of an acid catalyst having a pK value of at most 4 at a temperature within the range from about 100° to about 180° C. until the corresponding acid is formed.

52. A process according to claim 51 in which the mercaptide is selected from the group consisting of α- and β-mercaptocarboxylic acid esters, mercaptoalcohol esters and aryl mercaptans.

53. A process according to claim 51 in which the reaction is carried out under reflux in the presence of an inert organic solvent boiling at a temperature within the range from about 100° to about 180° C.

54. A process according to claim 51 in which the acid catalyst is selected from the group consisting of hydrobromic acid, hydrochloric acid, formic acid, methanesulfonic acid, oxalic acid, phosphoric acid, phosphorous acid, perchloric acid, sulfuric acid, thiodiacetic acid, chloroacetic acid, cyclohexylidenebis (thioacetic acid), cyclohexen-1-yl thioacetic acid, and citric acid.

55. A process according to claim 51 in which the temperature is within the range from about 100° to about 140° C.

56. A process according to claim 52 in which an excess of mercaptide is used to aid in driving the reaction to completion.

* * * * *